United States Patent
Barkai et al.

(10) Patent No.: US 9,540,630 B2
(45) Date of Patent: Jan. 10, 2017

(54) OPTIMIZATION OF ALGINATE ENCAPSULATION OF ISLETS FOR TRANSPLANTATION

(75) Inventors: Uriel Barkai, Holf-Carmel (IL); Avi Rotem, Petach Tikva (IL); Dimitry Azarov, Petach Tikva (IL); Tova Neufeld, Ariel (IL); Zohar Gendler, Zichron Ya'akov (IL)

(73) Assignee: BETA O2 TECHNOLOGIES LTD., Petach Tikva (IL)

( * ) Notice: Subject to any disclaimer, the term of this patent is extended or adjusted under 35 U.S.C. 154(b) by 669 days.

(21) Appl. No.: 12/996,592

(22) PCT Filed: Sep. 16, 2009

(86) PCT No.: PCT/IL2009/000905
§ 371 (c)(1),
(2), (4) Date: Jan. 13, 2011

(87) PCT Pub. No.: WO2010/032242
PCT Pub. Date: Mar. 25, 2010

(65) Prior Publication Data
US 2011/0165219 A1    Jul. 7, 2011

Related U.S. Application Data

(60) Provisional application No. 61/192,412, filed on Sep. 17, 2008.

(51) Int. Cl.
*C12N 5/071* (2010.01)
*C12N 11/04* (2006.01)
*C12N 11/10* (2006.01)

(52) U.S. Cl.
CPC ............. *C12N 11/10* (2013.01); *C12N 5/0677* (2013.01); *C12N 11/04* (2013.01)

(58) Field of Classification Search
USPC .................................................. 435/325, 382
See application file for complete search history.

(56) References Cited

U.S. PATENT DOCUMENTS

| | | | |
|---|---|---|---|
| 2,564,977 A | 8/1951 | Hu | |
| 4,352,883 A | 10/1982 | Lim | |
| 4,402,694 A | 9/1983 | Ash et al. | |
| 4,631,053 A | 12/1986 | Taheri et al. | |
| 4,673,566 A | 6/1987 | Goosen et al. | |
| 4,721,677 A | 1/1988 | Clark, Jr. | |
| 4,801,291 A | 1/1989 | Loori | |
| 4,997,443 A | 3/1991 | Walthall et al. | |
| 5,002,661 A | 3/1991 | Chick et al. | |
| 5,011,472 A | 4/1991 | Aebischer et al. | |
| 5,015,476 A | 5/1991 | Cochrum et al. | |
| 5,029,579 A | 7/1991 | Trammell | |
| 5,101,814 A | 4/1992 | Palti | |
| 5,116,493 A | 5/1992 | Chick et al. | |
| 5,116,494 A | 5/1992 | Chick et al. | |
| 5,262,055 A * | 11/1993 | Bae et al. ............... | 210/645 |
| 5,336,209 A | 8/1994 | Porzilli | |
| 5,381,075 A | 1/1995 | Jordan | |
| 5,407,685 A | 4/1995 | Malchesky et al. | |
| 5,427,935 A | 6/1995 | Wang et al. | |
| 5,443,508 A | 8/1995 | Giampapa | |
| 5,529,066 A | 6/1996 | Palti | |
| 5,578,022 A | 11/1996 | Scherson et al. | |
| 5,578,314 A | 11/1996 | Cochrum | |
| 5,614,378 A | 3/1997 | Yang et al. | |
| 5,639,275 A | 6/1997 | Baetge | |
| 5,662,625 A | 9/1997 | Westwood | |
| 5,702,444 A | 12/1997 | Struthers et al. | |
| 5,713,888 A | 2/1998 | Neuenfeldt et al. | |
| 5,741,334 A | 4/1998 | Mullon et al. | |
| 5,788,682 A | 8/1998 | Maget | |
| 5,792,090 A | 8/1998 | Ladin | |
| 5,800,828 A | 9/1998 | Dionne et al. | |
| 5,834,005 A | 11/1998 | Usala | |
| 5,855,570 A | 1/1999 | Scherson et al. | |
| 5,855,613 A | 1/1999 | Antanavich et al. | |
| 5,879,709 A | 3/1999 | Soon-Shoing et al. | |
| 5,902,745 A | 5/1999 | Butler et al. | |
| 5,912,005 A | 6/1999 | Lanza et al. | |
| 6,000,403 A | 12/1999 | Cantwell | |
| 6,091,974 A | 7/2000 | Palti | |
| 6,148,232 A | 11/2000 | Avrahami | |
| 6,165,225 A * | 12/2000 | Antanavich ............ | A61F 2/022 623/23.72 |

(Continued)

FOREIGN PATENT DOCUMENTS

GB  2024012      1/1980
JP  6-507412 A   8/1994

(Continued)

OTHER PUBLICATIONS

Suzuki et al. Function and survival of macroencapsulated synergenic islets transplanted into streptozocin-diabetic mice. Transplantation, vol. 66 No. 1 (Jul. 15, 1998) pp. 21-28.*
Mørch et al., Effect of Ca2+, Ba2+, and Sr2+ on alginate microbeads. Biomacromolecules, vol. 7 (2006) pp. 1471-1480.*
Huang et al., A replacement for islet equivalents with improved reliability and validity. Acta Diabetologica, (online Feb. 3, 2012).*
Casavilla et al., Laparoscopic approach for islet cell transplantation. Transplant Proceedings, Vo;. 24 No. 6 (1992) p. 2800.*
Nagata et al., Co-culture of extracellular matrix suppresses the cell death of rat pancreatic islets. Journal of Biomaterials Science Polymer Edition, vol. 13 No. 5 (2002) pp. 579-590.*
Itakura et al., Mesenchymal stem cells facilitate the induction of mixed hematopoietic chimerism and islet allograft tolerance without GVHD in the rat. American Journal of Transplantation, vol. 7 No. 2 (2007) pp. 336-346.*

(Continued)

Primary Examiner — Kara Johnson
(74) Attorney, Agent, or Firm — Greenberg Traurig, LLP

(57) ABSTRACT

Apparatus is provided, including a plurality of islets, and a hydrogel configured to macroencapsulate the plurality of islets. The hydrogel is implantable in a subcapsular space (21) of a kidney (22) of a subject and is shaped to define a planar configuration. Other applications are also described.

16 Claims, 9 Drawing Sheets

(56) References Cited

U.S. PATENT DOCUMENTS

| | | | |
|---|---|---|---|
| 6,179,804 | B1 | 1/2001 | Satterfield |
| 6,268,161 | B1 | 7/2001 | Han et al. |
| 6,368,592 | B1 | 4/2002 | Colton et al. |
| 6,372,244 | B1 | 4/2002 | Antanavich et al. |
| 6,383,478 | B1 | 5/2002 | Prokop et al. |
| 6,432,449 | B1 | 8/2002 | Goldenberg et al. |
| 6,630,154 | B1 | 10/2003 | Fraker et al. |
| 6,767,342 | B1 | 7/2004 | Cantwell |
| 6,815,186 | B2 | 11/2004 | Clark, Jr. et al. |
| 6,821,107 | B1 | 11/2004 | Hara et al. |
| 6,960,351 | B2 | 11/2005 | Dionne et al. |
| 7,361,333 | B2 | 4/2008 | Latta |
| 7,892,222 | B2 | 2/2011 | Vardi |
| 8,012,500 | B2 | 9/2011 | Rotem |
| 8,043,271 | B2 | 10/2011 | Stern |
| 8,444,630 | B2 | 5/2013 | Roten et al. |
| 2002/0022016 | A1 | 2/2002 | Walsh et al. |
| 2003/0050622 | A1 | 3/2003 | Humes et al. |
| 2003/0087427 | A1 | 5/2003 | Colton et al. |
| 2003/0113302 | A1 | 6/2003 | Revazova et al. |
| 2004/0133188 | A1 | 7/2004 | Vardi et al. |
| 2004/0178358 | A1 | 9/2004 | Kreiss et al. |
| 2005/0025680 | A1 | 2/2005 | Monzyk et al. |
| 2005/0136092 | A1 | 6/2005 | Rotem et al. |
| 2006/0024276 | A1 | 2/2006 | Ricordi |
| 2006/0035370 | A1 | 2/2006 | Lee et al. |
| 2006/0063140 | A1 | 3/2006 | Nussinovitch |
| 2007/0190038 | A1 | 8/2007 | Suzuki |
| 2008/0086042 | A1 | 4/2008 | Brister et al. |
| 2009/0012502 | A1 | 1/2009 | Rotem et al. |
| 2010/0047311 | A1 | 2/2010 | Rotem |
| 2010/0130916 | A1 | 5/2010 | Stern |
| 2010/0312165 | A1 | 12/2010 | Stern |
| 2011/0165219 | A1 | 7/2011 | Barkai |
| 2011/0300191 | A1 | 12/2011 | Barkai et al. |

FOREIGN PATENT DOCUMENTS

| | | |
|---|---|---|
| JP | 8-512282 A | 12/1996 |
| WO | 86/03781 | 7/1986 |
| WO | 90/15526 | 12/1990 |
| WO | 92/19195 | 11/1992 |
| WO | 92/19195 A1 | 11/1992 |
| WO | 94/20076 | 9/1994 |
| WO | 94/20076 A1 | 9/1994 |
| WO | 00/78920 | 12/2000 |
| WO | 01/50983 | 7/2001 |
| WO | 02/24107 | 3/2002 |
| WO | 03/011445 | 2/2003 |
| WO | 2005/063147 | 7/2005 |
| WO | 2006/059322 | 6/2006 |
| WO | 2007/138590 | 12/2007 |
| WO | 2007/144389 | 12/2007 |
| WO | 2008/027420 | 3/2008 |
| WO | 2008/062417 | 5/2008 |
| WO | 2008/065660 | 6/2008 |
| WO | 2008/079997 A2 | 7/2008 |
| WO | 2008/112190 | 9/2008 |
| WO | 2009/031154 | 3/2009 |
| WO | 2010/032242 | 3/2010 |
| WO | 2010/032242 A1 | 3/2010 |
| WO | 2010/061387 | 6/2010 |
| WO | 2011/154941 A2 | 12/2011 |

OTHER PUBLICATIONS

Kin et al., Survival and metabolic function of syngeneic rat islet grafts transplanted in the omental pouch. American Journal of Transplantation, vol. 3 (2003) pp. 281-285.*

Freshney, R. Ian., Culture of Animal Cells: A Manual of Basic Technique and Specialized Applications. Sixth ed. John Wiley & Sons, Inc., Hoboken, NJ (2010) Chps 20 and 22. 2010.*

Kent et al., Species variation and the success of endothelial cell seeding. Journal of Vascular Surgery, vol. 9, No. 2 (Feb. 1989) pp. 271-276.*

Office Action dated Mar. 2, 2012, issued in Japanese Patent Application No. JP 2007-544006.

Office Action dated Apr. 24, 2012, issued in U.S. Appl. No. 12/064,946.

International Search Report dated Jan. 25, 2012 issued in PCT/IL2011/00445.

English translation of Office Action dated Dec. 8, 2011, issued in Chinese Application No. CN 200580047325.4.

U.S. Appl. No. 61/192,412, filed Sep. 17, 2008.

U.S. Appl. No. 61/351,992, filed Jun. 7, 2010.

Andresen I-L et al. "Some biological functions of matrix components in benthic algae in relation to their chemistry and the composition of seawater," ACS Symp. Ser. 48:361-381 (1977). Abstract only.

Brissova M et al. "Control and measurement of permeability for design of microcapsule cell delivery system," J Biomed Mater Res, 39:61-70 (1998) Abstract only.

An office Action dated Jan. 7, 2011, which issued during the prosecution of Applicant's U.S. Appl. No. 11/001,556.

An Interview Summary dated Feb. 28, 2011, which issued during the prosecution of Applicant's U.S. Appl. No. 11/001,556.

An office Action dated Dec. 2, 2013, which issued during the prosecution of Applicant's U.S. Appl. No. 12/676,744.

Papas K.K. et al.: "High-Density Culture of Human Islets on Top of Silicone Rubber Membranes," Transplantation Proceedings, 37, 3412-3414 (2005).

Dulong, Jean-Luc: "A Theoretical Study of Oxygen Transfer Including Cell Necrosis for the Design of a Bioartificial Pancreas," Biotechnologies and Bioengineering, vol. 96, No. 5, Apr. 1, 2007.

Wu H et al., "In-situ electrochemical oxygen generation with an immunoisolation device", Ann N Y Acad Sci 875:105-25 (1999).

L. Leheninger, Biochemistry, Worth Publishers, Inc. 1978, Chapter 14, pp. 363-364.

Smith AJ, "Acetate assimilation by nitrobacter agilis in relation to its 'obligate autotrophy'", Journal of Bacteriology 95:844 (1968).

Klueh, et al., "Enhancement of implantable glucose sensor function in vivo using gene transfer-induced neovascularization", Biomaterials, vol. 26, No. 10, Apr. 2005. (an abstract).

Silva AI et al., "An overview on the development of a bio-artificial pancreas as a treatment of insulin-dependent diabetes mellitus," Med Res Rev 26 (2):181-222 (2006).

Faithful, N. S. Anaesthesia, 42, pp. 234-242 (1987).

Lacy PE et al., "Maintenance of normoglycemia in diabetic mice by subcutaneous xenografts of encapsulated islets," Science 1782-4 (1991).

Kaisers U et al., "Liquid ventilation," British Journal of Anaesthesia 91 (1) : 143-151 (2003).

Lorch H et al., "Central venous access ports placed by interventional radiologists: experience with 125 consecutive patients", Journal CardioVascular and interventional radiology, pp. 180-184, Issue vol. 24, No. 3 (2001).

Stagner, et al., "The pancreas as an islet transplantation site", Sep. 1, 2007, Journal of the Pancreas, vol. 8, No. 5, pp. 628-636.

An International Search Report and a Written opinion both dated Jan. 25, 2010, which issued during the prosecution of Applicant's PCT/IL09/00905.

Waschke KF, et al., "Modified haemolglobins and perfluorocarbons" (Current opinion in Anaesthesiology. 12(2): 195-202 (1999).

An office Action dated May 14, 2010, which issued during the prosecution of Applicant's U.S. Appl. No. 12/315,102.

An office Action dated Jun. 22, 2010, which issued during the prosecution of Applicant's U.S. Appl. No. 10/466,069.

A Written Opinion dated Oct. 1, 2008, which issued during the prosecution of Applicant's PCT/IL07/01471.

An International Preliminary Report on Patentability dated Jun. 30, 2009, which issued during the prosecution of Applicant's PCT/IL07/01471.

A Written Opinion dated Feb. 5, 2009, which issued during the prosecution of Applicant's PCT/IL08/01204.

(56) References Cited

OTHER PUBLICATIONS

An International Preliminary Report on Patentability dated Mar. 9, 2010, which issued during the prosecution of Applicant's PCT/IL08/01204.
An office Action dated Sep. 8, 2010, which issued during the prosecution of Applicant's U.S. Appl. No. 12/151,102.
A Notice of Allowance dated Jul. 11, 2011, which issued during the prosecution of Applicant's U.S. Appl. No. 12/151,102.
An office Action dated May 14, 2012, which issued during the prosecution of Applicant's U.S. Appl. No. 12/151,818.
An International Preliminary Report on Patentability dated May 31, 2011, which issued during the prosecution of Applicant's PCT/IL09/01114.
A Restriction Requirement dated Jul. 31, 2013, which issued during the prosecution of Applicant's U.S. Appl. No. 12/676,744.
An office Action dated Apr. 24, 2012, which issued during the prosecution of Applicant's U.S. Appl. No. 12/646,946.
An office Action dated Dec. 16, 2012, which issued during the prosecution of Applicant's U.S. Appl. No. 12/646,946.
A Notice of Allowance dated Jan. 22, 2013, which issued during the prosecution of Applicant's U.S. Appl. No. 12/646,946.
A Notice of Allowance dated Mar. 20, 2013, which issued during the prosecution of Applicant's U.S. Appl. No. 12/646,946.
A Written Opinion dated Oct. 1, 2008, which issued during the prosecution of Applicant's PCT/IL07/01447.
An International Preliminary Report on Patentability dated May 26, 2009, which issued during the prosecution of Applicant's PCT/IL07/01447.
Axen KV and Pi-Sunyer FX "Reversal of streptozotocin-induced diabetes in rats by intramuscular implantation of cultured islets," Transplantation 31: 439-441 (1981). Abstract.
Clayton HA et al., "The effect of capsule composition on the biocompatibility of alginate-poly-l-lysine capsules," J Microencapsul. 8(2):221-33 (1991).
Constantinidis I et al., "Effects of alginate composition on the metabolic, secretory, and growth characteristics of entrapped beta TC3 mouse insulinoma cells," Biomaterials 20(21):2019-27 (1999).
Cruise GM et al., "In vitro and in vivo performance of porcine islets encapsulated in interfacially photopolymerized poly (ethylene glycol) diacrylate membranes," Cell Transplant 8 : 293-306 (1999).
De Vos P et al., "Alginate-based microcapsules for immunoisolation of pancreatic islets," Biomaterials 27, 5603-5617 (2006).
Dufrane D et al., "Six-month survival of microencapsulated pig islets and alginate biocompatibility in primates: Proof of concept," Transplantation. 81:1345-1353 (2006).
Elliott RB et al., "Intraperitoneal alginate-encapsulated neonatal porcine islets in a placebo-controlled study with 16 diabetic cynomolgus primates," Transplant Proc 37:3505-8 (2005).
Cole DR et al., "Transplantation of microcapsules (a potential bio-artificial organ): biocompatibility and host reaction," Journal of Materials Science: Materials in Medicine vol. 4, No. 5, pp. 437-442 (1993).
Elliott RB et al., "Live encapsulated porcine islets from a type 1 diabetic patient 9.5 yr after xenotransplantation," Xenotransplantation vol. 14, Issue 2, pp. 157-161 (2007).
Hara Y et al., "Influence of the numbers of islets on the models of rat syngeneic-islet and allogeneic-islet transplantations," Transplantation proceedings vol. 38, No. 8, pp. 2726-2728 (2006).
Inuma IM and Mardi AS et al., "Pancreatic islet number and volume weighted mean volume in weanling and young Wistar Kyoto rats," J Anat 205: 541-542 (2004).
Juang JH et al., "Islet transplantation at subcutaneous and intramuscular sites," Transplant Proc. 37:3479-81 (2005).
Kim YY et al., "Improved phenotype of rat islets in a macrocapsule by co-encapsulation with cross-linked Hb," J. Biomater. Sci. Polym. Ed., 16, 1521-1535 (2005).
Larsen JL et al., "Tacrolimus and sirolimus cause insulin resistance in normal sprague dawley rats," Transplantation. 82(4):466-70 (2006).

Lim F and Sun A, "Microencapsulated Islets as Bioartificial Endocrine Pancreas," Science, 210:908-910 (1980).
Gazda LS et al., "Encapsulation of porcine islets permits extended culture time and insulin independence in spontaneously diabetic BB rats," Cell Transplant 16(6):609-20 (2007).
Maria-Engler SS et al., "Microencapsulation and tissue engineering as an alternative treatment of diabetes," Braz J Med Biol Res, vol. 34(6) 691-697 (2001).
Matsumoto S et al., "Insulin independence after living-donor distal pancreatectomy and islet allotransplantation," Lancet. 365:1642-4 (2005).
Napoli R et al., "Islet transplantation under the kidney capsule fully corrects the impaired skeletal muscle glucose transport system of streptozocin diabetic rats," J. Clin. Invest. 97(6): 1389-1397 (1996).
Narang AS et al., "Biological and biomaterial approaches for improved islet transplantation," Pharmacol Rev 58:194-243 (2006).
O'Connell PJ et al, "Clinical islet transplantation in type 1 diabetes mellitus: results of Australia's first trial," MJA, vol. 184 No. 5 pp. 221-225 (2006).
Qi M et al., "PVA hydrogel sheet for macroencapsulation for the bioartificial pancreas," Biomaterials 25(27):5885 (2004).
Rafael E et al., "Intramuscular autotransplantation of pancreatic islets in a 7-year-old child: A 2-year follow-up," Am J Transplant 8: 458-462 (2008).
Rappel MJ, "Maintaining islet quality during culture," a thesis published in the Massachusetts Institute of Technology. Dept. of Chemical Engineering. (2007).
Reach G et al., "A U-shaped bioartificial pancreas with rapid glucose-insulin kinetics. In vitro evaluation and kinetic modelling," Diabetes 33:752-761 (1984).
Matarazzo M et al., "Islet Transplantation Under the Kidney Capsule Corrects the Defects in Glycogen Metabolism in Both Liver and Muscle of Streptozocin-Diabetic Rats," Cell Transplantation, vol. 11, pp. 103-112 (2002).
Schaffellner S et al., "Porcine islet cells microencapsulated in sodium cellulose sulfate," Transplant Proc, 37:248-252 (2005).
Shapiro AM et al., "Islet transplantation in seven patients with type 1 diabetes mellitus using a glucocorticoid-free immunosuppressive regimen," N Engl J Med 343:230-8 (2000).
Simpson NE et al., "Effects of growth regulation on conditionally-transformed alginate-entrapped insulin secreting cell lines in vitro," Biomaterials vol. 26, Issue 22 pp. 4633-4641 (2005).
Rickels MR et al., "Evidence for allograft rejection in an islet transplant recipient and effect on beta-cell secretory capacity," J Clin Endocrinol Metab. 92:2410-4 (2007).
Ricordi C et al., "Low-temperature culture of human islets of in vivo treatment L3T4 antibody produces a marked prolongation of islet human-to-mouse xenograft survival," Proc. Natl. Acad. Sci. USA, 84:8080-84 (1987).
Risbud MV et al., "In vivo biocompatibility evaluation of cellulose macrocapsules for islet immunoisolation: Implications of low molecular weight cut-off," J Biomed Mater Res 66 : 86-92 (2003).
Ryan EA et al., "Five-year follow-up after clinical islet transplantation," Diabetes, 54:2060-9 (2005).
Tatarkiewicz K et al., "Reversal of hyperglycemia in mice after subcutaneous transplantation of macroencapsulated islets transplantation," vol. 67(5)15 pp. 665-671 (1999).
Storrs R et al., "Preclinical development of the islet sheet," Ann N Y Acad Sci. 944:252-66 (2001).
Valdes-Gonzalez RA et al., "Three-yr follow-up of a type 1 diabetes mellitus patient with an islet xenotransplant," Clinical Transplantation, vol. 21 Issue 3, pp. 352-357 (2007).
Valdes-Gonzalez RA et al., "Xenotransplantation of porcine neonatal islets of Langerhans and Sertoli cells: a 4-year study," Eur J Endocrinol 153: 419-427 (2005).
Wahoff DC et al., "Free intraperitoneal islet autografts in pancreatectomized dogs—Impact of islet purity and post-transplantation exogenous insulin," Surgery 116:742-750 (1994).
Zekorn T et al. "Alginate coating of islets of Langerhans: in vitro studies on a new method for microencapsulation for immunoisolated transplantation," Acta Diabetol 29:41-45(1992).

(56) References Cited

OTHER PUBLICATIONS

Zekorn T et al. Islet transplantation in immunoseparating membranes for treatment of insulin-dependent diabetes mellitus, Exp Clin Endocrinol Diabetes 103 (Suppl 2):136-139 (1995).

Zekorn TD et al., "Biocompatibility and immunology in the encapsulation of islets of Langerhans (bioartificial pancreas)," Int J Artif Organs 19:251-257 (1996).

Zimmermann H et al., "Alginate-based Encapsulation of Cells: Past, Present, and Future," Curr Diab Rep. 7 (4):314-20 (2007).

Francis-Floyed Ruth, Dissolved oxygen for fish production; Feb. 2003, University of Florida; http://edis.ifas.ufl.edu/fa002.

Stabler C et al., in an article entitled, "The effects of alginate composition on encapsulated βTC3 cells," (Biomaterials vol. 22, No. 11, pp. 1301-1310 (2001).

Cheng SY et al., in an article entitled, "Insulin secretion dynamics of free and alginate-encapsulated insulinoma cells," (Cytotechnology 51:159-170 (2006).

Reach G, "Bioartificial pancreas. Present state and future prospects," Biomed Biochim Acta 43: 569-576 (1984).

Shapiro AM et al., "International multicenter trial of islet transplantation using the edmonton protocol in patients with type I diabetes," Am J Transplantation 3 (Suppl 5):152 (2003).

"Bioartificial Organs II: Conference Report," co-sponsored by The Engineering Foundation and the Juvenile Diabetes Foundation International, from a conference held in Banff, Alberta, Canada, Jul. 18-22, 1998.

Office Action dated Jul. 18, 2013, issued in U.S. Appl. No. 13/153,721.

An Office Action dated Mar. 13, 2014, which issued during the prosecution of U.S. Appl. No. 13/153,721.

Supplementary European Search Report dated Apr. 22, 2014 which issued during the prosecution of Applicant's European App No. 09 82 8728.

* cited by examiner

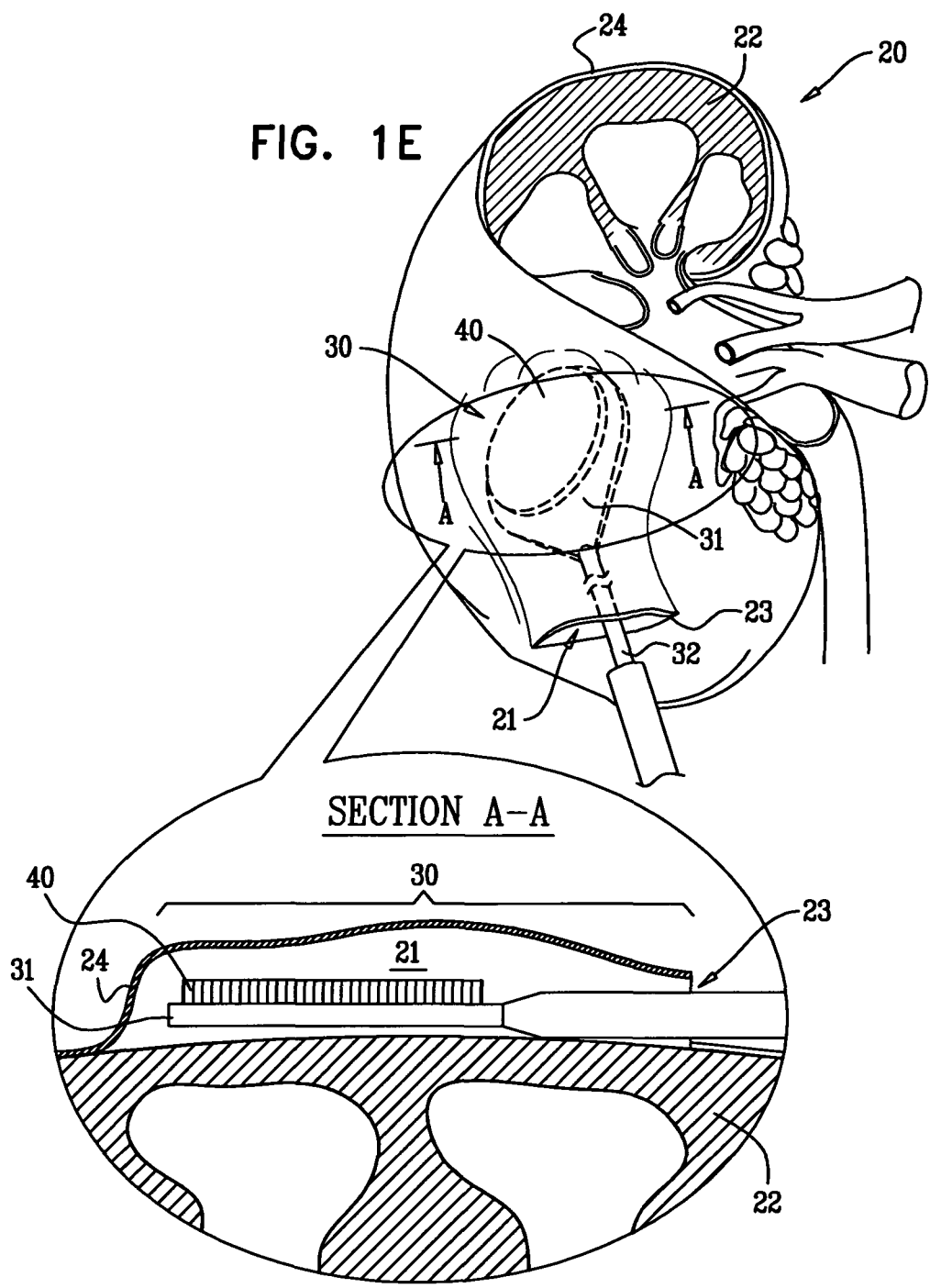

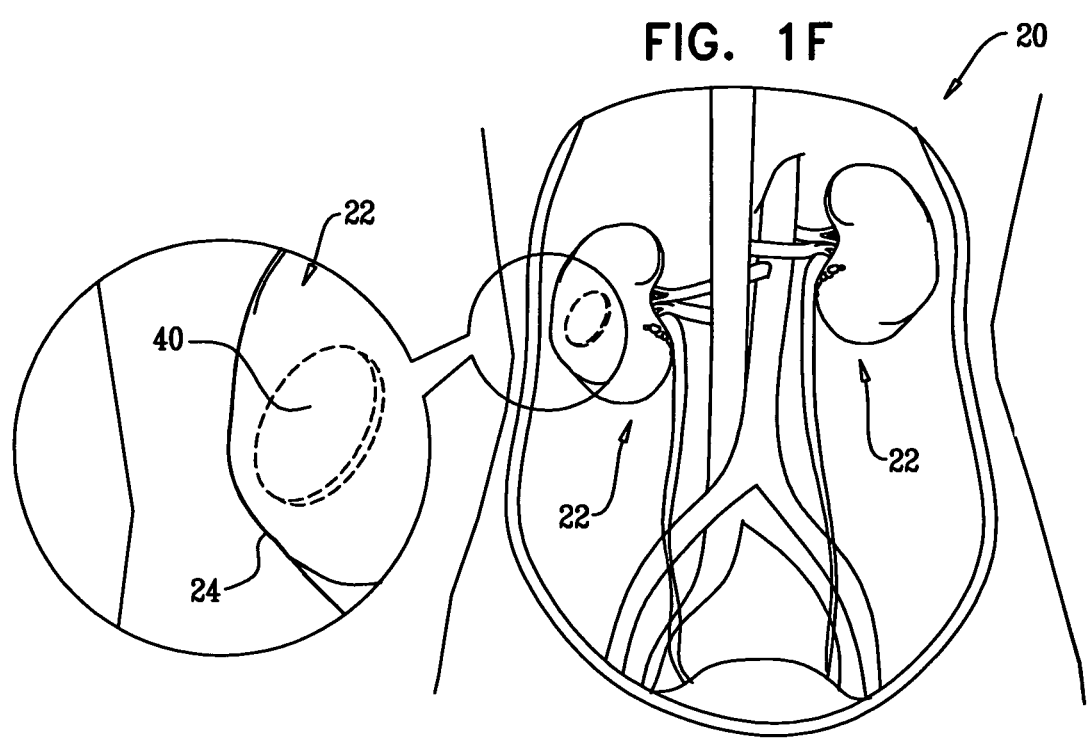

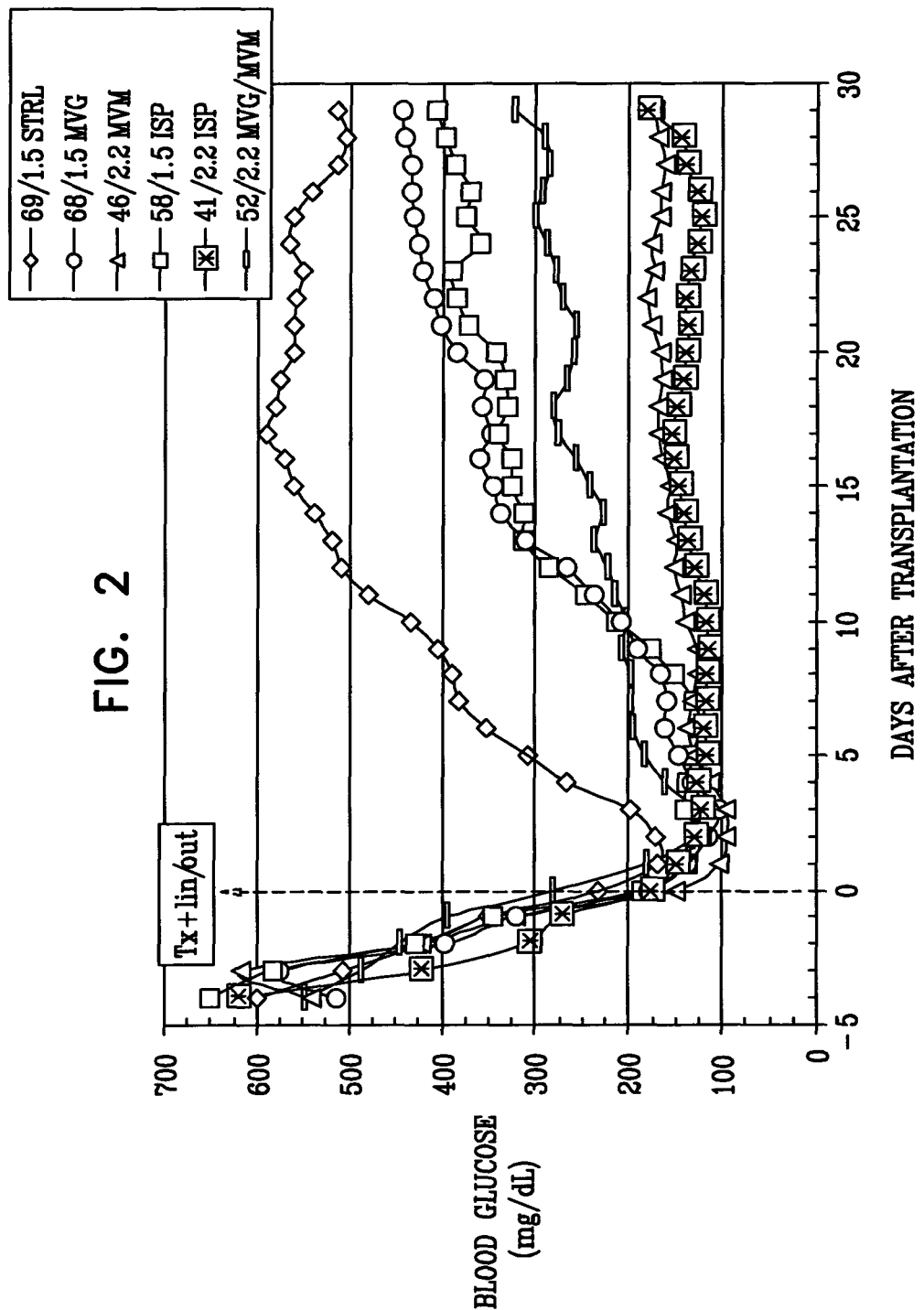

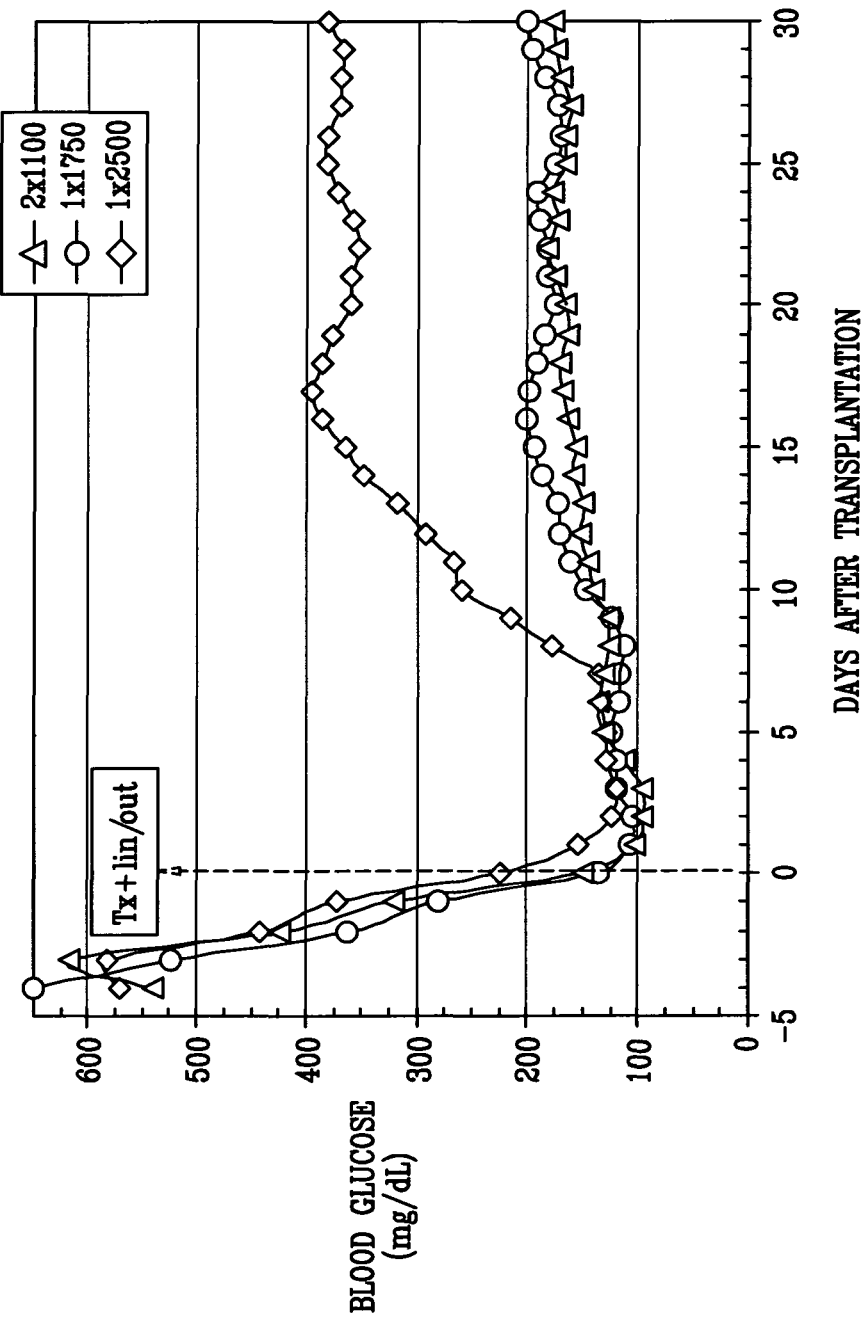

OPTIMIZATION OF ALGINATE ENCAPSULATION OF ISLETS FOR TRANSPLANTATION

CROSS-REFERENCES TO RELATED APPLICATIONS

The present application is a U.S. national phase of PCT Application no. PCT/IL2009/000905 to Barkai et al., filed Sep. 16, 2009, which claims priority from U.S. Provisional Patent Application 61/192,412 to Barkai et al., entitled, "Optimization of alginate encapsulation of islets for transplantation," filed Sep. 17, 2008, which is incorporated herein by reference.

FIELD OF THE INVENTION

Some applications of the present invention relates in general to encapsulation of islets. More specifically, some applications of the present invention relates to alginate encapsulation of islets to be transplanted within a body of a subject.

BACKGROUND OF THE INVENTION

Oxygen is essential to many physiological and metabolic processes, including aerobic metabolism. A lack of oxygen for implanted cells often leads to cell injury or death. Oxygen provision is a vital component in sustaining transplanted cells.

The success of many transplants is compromised not only due to graft-host rejections, but also by ischemic conditions generated by insufficient oxygen supply to the transplant. Following implantation of the cells, oxygen can be provided to the implanted cells from the body tissue (mainly via diffusion). However, the natural diffusion rate is too low in order to provide the cells with a significant, necessary amount of oxygen amount.

Islet transplantation in experimental models is conducted under the influence of immunosuppressive drugs. Such immunosuppression is typically associated with adverse effects such as increased infection and malignancy rates. Additionally, the immunosuppressive drugs are known to affect the viability and the functionality of the transplanted islets and to trigger insulin resistance in the animal model.

Islets have been microencapsulated in various polymeric hydrogel matrices including alginate, acrylic acid derivatives, polyethylene glycol (PEG) conformal micro-coatings, nanocoatings, cellulose, and/or agarose. Microencapsulated islets are typically transplanted within the peritoneal space, but have also been implanted within the liver, the spleen, and the subcapsular space of the kidney. Microencapsulating islets provides a low ratio (typically about 1:100) of (a) the volume of islets to (b) the volume of alginate hydrogel (i.e., capsule). The subcapsular space of the kidney cannot sufficiently support the relatively large volume of alginate microcapsules.

U.S. Pat. No. 6,165,225 to Antanavich et al. describes bioartificial implants and methods for their manufacture and use, particularly bioartificial pancreases. In particular, the implants may be thin sheets which enclose cells, may be completely biocompatible over extended periods of time and may not induce fibrosis. The high-density-cell-containing thin sheets are preferably completely retrievable, and have dimensions allowing maintenance of optimal tissue viability through rapid diffusion of nutrients and oxygen and also allowing rapid changes in the secretion rate of insulin and/or other bioactive agents in response to changing physiology. Implantations of living cells, tissue, drugs, medicines and/or enzymes, contained in the bioartificial implants may be made to treat and/or prevent disease.

PCT Publication WO 07/144389 to Durfane et al. describes cellular devices comprising a collagen matrix, cell layer, and gelled alginate layer, processes for producing the devices, methods of implanting the devices, and methods of treatment thereof.

In a conference report entitled, "Bioartificial Organs II: Conference Report," co-sponsored by The Engineering Foundation and the Juvenile Diabetes Foundation International, from a conference held in Banff, Alberta, Canada, Jul. 18-22, 1998, the portion relating to a bioartificial pancreas described the use of "medium-sized capsules" of 350 μm. This would correspond to a transplant volume of 35 mL for a 70 kg individual. A five-month diabetes reversal in dogs was observed in transplantation of the capsules in the peritoneum or omental pouch.

U.S. Pat. No. 6,960,351 to Dionne describes an immunoisolatory vehicle for the implantation into an individual of cells which produce a needed product or provide a needed metabolic function. The vehicle is comprised of a core region containing isolated cells and materials sufficient to maintain the cells, and a permselective, biocompatible, peripheral region free of the isolated cells, which immunoisolates the core yet provides for the delivery of the secreted product or metabolic function to the individual. The vehicle is described as being particularly well-suited to delivery of insulin from immunoisolated islets of Langerhans, and can also be used for delivery of high molecular weight products, such as products larger than IgG. A method of making a biocompatible, immunoisolatory implantable vehicle is described, consisting in a first embodiment of a coextrusion process, and in a second embodiment of a stepwise process. A method is also described for isolating cells within a biocompatible, immunoisolatory implantable vehicle, which protects the isolated cells from attack by the immune system of an individual in whom the vehicle is implanted. A method is provided for providing a needed biological product or metabolic function to an individual, comprising implanting into the individual an immunoisolatory vehicle containing isolated cells which produce the product or provide the metabolic function.

PCT Publication WO 01/50983 to Vardi et al., and U.S. patent application Ser. No. 10/466,069 in the national phase thereof, which are assigned to the assignee of the present application and are incorporated herein by reference, describe an implantable device comprising a chamber for holding functional cells and an oxygen generator for providing oxygen to the functional cells. In one embodiment, the oxygen generator is described as comprising photosynthetic cells that convert carbon dioxide to oxygen when illuminated. In another embodiment, the oxygen generator is described as comprising electrodes that produce oxygen by electrolysis.

Stabler C et al., in an article entitled, "The effects of alginate composition on encapsulated βTC3 cells," (Biomaterials vol. 22, no 11, pp. 1301-1310 (2001)), describe the effects of alginate composition on the growth of murine insulinoma βTC3 cells encapsulated in alginate/poly-L-lysine/alginate (APA) beads, and on the overall metabolic and secretory characteristics of the encapsulated cell system for four different types of alginate. Two of the alginates used had a high guluronic acid content (73% in guluronic acid residues) with varying molecular weight, while the other two had a high mannuronic acid content (68% in mannuronic acid residues) with varying molecular weight. Each composition was tested using two different polymer concentrations. Their data show that βTC3 cells encapsulated in alginates with a high guluronic acid content experienced a transient hindrance in their metabolic and secretory activity because of growth inhibition. Conversely, βTC3 cells encapsulated in alginates with a high mannuronic acid content experienced a rapid increase in metabolic and secretory activity as a result of rapid cell growth. Their data also demonstrate that an increase in either molecular weight or concentration of high mannuronic acid alginates did not alter the behavior of the encapsulated βTC3 cells. Conversely, an increase in molecular weight and concentration of high guluronic acid alginates prolonged the hindrance of glucose metabolism, insulin secretion and cell growth. These observations were interpreted as resulting from changes in the microstructure of the alginate matrix, i.e., interaction between the contiguous guluronic acid residues and the Ca2 ions, as a result of the different compositions.

Cheng S Y et al., in an article entitled, "Insulin secretion dynamics of free and alginate-encapsulated insulinoma cells," (Cytotechnology 51:159-170 (2006)), describe the effect of alginate/poly-1-lysine/alginate (APA) encapsulation on the insulin secretion dynamics exhibited by an encapsulated cell system. Experiments were performed with the aid of a home-built perfusion apparatus providing 1 min temporal resolution. Insulin profiles were measured from: (i) murine insulinoma βTC3 cells encapsulated in calcium alginate/poly-1-lysine/alginate (APA) beads generated with high guluronic (G) or high mannuoric (M) content alginate, and (ii) murine insulinoma βTC-tet cells encapsulated in high M APA beads and propagated in the presence and absence of tetracycline. Results show that encapsulation in APA beads did not affect the insulin secretion profile shortly post-encapsulation. However, remodeling of the beads due to cell proliferation affected the insulin secretion profiles; and inhibiting remodeling by suppressing cell growth preserved the secretion profile. The implications of these findings regarding the in vivo function of encapsulated insulin secreting cells are discussed.

PCT Publication WO 86/03781 to Larsen et al. describes a process for producing alginates having improved physical properties, by the inoculation of alginates derived from brown algae or bacteria, with an enzyme preparation such as a mannuronan-C-5-epimerase preparation from *Azotobacter vinelandii*. The modified alginates are used for immobilizing enzymes, cell organelles or cells as well as for the microencapsulation of biocatalysts.

PCT Publication WO 02/024107 to Dorain et al. describes a method for making a physiologically active and biocompatible cellular implant for implantation into a host body. The method includes the steps of: (a) forming first and second layers of first and second polymer solutions, respectively, each layer having a first substantially uncross-linked surface and an opposing second cross-linked surface; (b) forming a sandwich of a cell suspension layer of physiologically active cells in a substantially uncross-linked third solution between the first and second, and (c) cross-linking the first and second polymer solutions in a direction toward the cell suspension layer, thereby forming a cellular implant. In another embodiment, all polymer solutions initially are uncross-linked and sequentially spread in layers followed by cross-linking.

The following references may be of interest:
PCT Publication WO 05/063147 to Wang et al.
PCT Publication WO 08/027420 to Kennedy et al.
U.S. Pat. No. 5,639,275 to Baetge
U.S. Pat. No. 6,368,592 to Colton et al.
U.S. Pat. No. 6,432,449 to Goldenberg et al
U.S. Pat. No. 6,960,351 to Dionne et al.
U.S. Pat. No. 7,361,333 to Latta
US Patent Application Publication 2005/0136092 to Rotem et al
Axen K V and Pi-Sunyer F X "Reversal of streptozotocin-induced diabetes in rats by intramuscular implantation of cultured islets," Transplantation 31: 439-441 (1981)
Clayton H A et al., "The effect of capsule composition on the biocompatibility of alginate-poly-1-lysine capsules," J Microencapsul. 8(2):221-33 (1991)
Cole D R et al., "Transplantation of microcapsules (a potential bio-artificial organ): biocompatibility and host reaction," Journal of Materials Science: Materials in Medicine Volume 4, Number 5, pp. 437-442 (1993)
Constantinidis I et al., "Effects of alginate composition on the metabolic, secretory, and growth characteristics of entrapped beta TC3 mouse insulinoma cells," Biomaterials 20(21):2019-27 (1999)
Cruise G M et al., "In vitro and in vivo performance of porcine islets encapsulated in interfacially photopolymerized poly (ethylene glycol) diacrylate membranes," Cell Transplant 8: 293-306 (1999)
de Vos P et al., "Alginate-based microcapsules for immunoisolation of pancreatic islets," Biomaterials 27, 5603-5617 (2006)
Dufrane D et al., "Six-month survival of microencapsulated pig islets and alginate biocompatibility in primates: Proof of concept," Transplantation. 81:1345-1353 (2006)
Elliott R B et al., "Intraperitoneal alginate-encapsulated neonatal porcine islets in a placebo-controlled study with 16 diabetic cynomolgus primates," Transplant Proc 37:3505-8 (2005)
Elliott R B et al., "Live encapsulated porcine islets from a type 1 diabetic patient 9.5 yr after xenotransplantation," Xenotransplantation Volume 14, Issue 2, Pages 157-161 (2007)
Gazda L S et al., "Encapsulation of porcine islets permits extended culture time and insulin independence in spontaneously diabetic BB rats," Cell Transplant 16(6):609-20 (2007)
Hara Y et al., "Influence of the numbers of islets on the models of rat syngeneic-islet and allogeneic-islet transplantations," Transplantation proceedings vol. 38, no. 8, pp. 2726-2728 (2006)
Inuma I M and Mardi A S et al., "Pancreatic islet number and volume weighted mean volume in weanling and young Wistar Kyoto rats," J Anat 205: 541-542 (2004)
Juang J H et al., "Islet transplantation at subcutaneous and intramuscular sites," Transplant Proc. 37:3479-81 (2005)
Kim Y Y et al., "Improved phenotype of rat islets in a macrocapsule by co-encapsulation with cross-linked Hb," J. Biomater. Sci. Polym. Ed., 16, 1521-1535 (2005)
Kin T et al., "Survival and metabolic function of syngeneic rat islet grafts transplanted in the omental pouch," Am. J. Transplant. 3, 281-285 (2003)
Larsen J L et al., "Tacrolimus and sirolimus cause insulin resistance in normal sprague dawley rats," Transplantation. 82(4):466-70 (2006)
Lim F and Sun A, "Microencapsulated Islets as Bioartificial Endocrine Pancreas," Science, 210:908-910 (1980)
Maria-Engler S S et al., "Microencapsulation and tissue engineering as an alternative treatment of diabetes," Braz J Med Biol Res, Volume 34(6) 691-697 (2001)
Matarazio M et al., "Islet Transplantation Under the Kidney Capsule Corrects the Defects in Glycogen Metabolism in Both Liver and Muscle of Streptozocin-Diabetic Rats," Cell Transplantation, Vol. 11, pp. 103-112 (2002)

Matsumoto S et al., "Insulin independence after living-donor distal pancreatectomy and islet allotransplantation," Lancet. 365:1642-4 (2005)

Napoli R et al., "Islet transplantation under the kidney capsule fully corrects the impaired skeletal muscle glucose transport system of streptozocin diabetic rats," J. Clin. Invest. 97(6): 1389-1397 (1996)

Narang A S et al., "Biological and biomaterial approaches for improved islet transplantation," Pharmacol Rev 58:194-243 (2006)

O'Connell P J et al, "Clinical islet transplantation in type 1 diabetes mellitus: results of Australia's first trial," MJA, Volume 184 Number 5 pp. 221-225 (2006)

Qi M et al., "PVA hydrogel sheet for macroencapsulation for the bioartificial pancreas," Biomaterials 25(27):5885 (2004)

Rafael E et al., "Intramuscular autotransplantation of pancreatic islets in a 7-year-old child: A 2-year follow-up," Am J Transplant 8: 458-462 (2008)

Rappel M J, "Maintaining islet quality during culture," a thesis published in the Massachusetts Institute of Technology. Dept. of Chemical Engineering. (2007)

Reach G et al., "A U-shaped bioartificial pancreas with rapid glucose-insulin kinetics. In vitro evaluation and kinetic modelling," Diabetes 33:752-761 (1984)

Reach G, "Bioartificial pancreas. Present state and future prospects," Biomed Biochim Acta 43: 569-576 (1984)

Rickels M R et al., "Evidence for allograft rejection in an islet transplant recipient and effect on beta-cell secretory capacity," J Clin Endocrinol Metab. 92:2410-4 (2007)

Ricordi C et al., "Low-temperature culture of human islets of in vivo treatment L3T4 antibody produces a marked prolongation of islet human-to-mouse xenograft survival," Proc. Natl. Acad. Sci. USA, 84:8080-84 (1987)

Risbud M V et al., "In vivo biocompatibility evaluation of cellulose macrocapsules for islet immunoisolation: Implications of low molecular weight cut-off," J Biomed Mater Res 66: 86-92 (2003)

Ryan E A et al., "Five-year follow-up after clinical islet transplantation," Diabetes, 54:2060-9 (2005)

Schaffellner S et al., "Porcine islet cells microencapsulated in sodium cellulose sulfate," Transplant Proc, 37:248-252 (2005)

Shapiro A M et al., "International multicenter trial of islet transplantation using the edmonton protocol in patients with type I diabetes," Am J Transplantation 3 (Suppl 5):152 (2003)

Shapiro A M et al., "Islet transplantation in seven patients with type 1 diabetes mellitus using a glucocorticoid-free immunosuppressive regimen," N Engl J Med 343:230-8 (2000)

Simpsona N E et al., "Effects of growth regulation on conditionally-transformed alginate-entrapped insulin secreting cell lines in vitro," Biomaterials Volume 26, Issue 22 pp. 4633-4641 (2005)

Storrs R et al., "Preclinical development of the islet sheet," Ann NY Acad Sci. 944:252-66 (2001)

Tatarkiewicz K et al., "Reversal of hyperglycemia in mice after subcutaneous transplantation of macroencapsulated islets transplantation," Volume 67(5)15 pp. 665-671 (1999)

Valdes-Gonzalez R A et al., "Three-yr follow-up of a type 1 diabetes mellitus patient with an islet xenotransplant," Clinical Transplantation, Volume 21 Issue 3, Pages 352-357 (2007)

Valdes-Gonzalez R A et al., "Xenotransplantation of porcine neonatal islets of Langerhans and Sertoli cells: a 4-year study," Eur J Endocrinol 153: 419-427 (2005)

Wahoff D C et al., "Free intraperitoneal islet autografts in pancreatectomized dogs—Impact of islet purity and post-transplantation exogenous insulin," Surgery 116:742-750 (1994)

Wang T et al., "Successful Allotransplantation of Encapsulated Islets in Pancreatectomized Canines for Diabetic Management Without the Use of Immunosuppression," Transplantation. 85:331-337 (2008)

Zekorn T et al. "Alginate coating of islets of Langerhans: in vitro studies on a new method for microencapsulation for immuno-isolated transplantation," Acta Diabetol 29:41-45 (1992)

Zekorn T et al. Islet transplantation in immunoseparating membranes for treatment of insulin-dependent diabetes mellitus," Exp Clin Endocrinol Diabetes 103 (Suppl 2):136-139 (1995)

Zekorn T D et al., "Biocompatibility and immunology in the encapsulation of islets of Langerhans (bioartificial pancreas)," Int J Artif Organs 19:251-257 (1996)

Zimmermann H et al., "Alginate-based Encapsulation of Cells: Past, Present, and Future," Curr Diab Rep. 7 (4):314-20 (2007)

SUMMARY OF THE INVENTION

In some applications of the present invention, cells encapsulated in various alginates having respective guluronic acid concentrations are designated for implantation in the subcapsular space of the kidney of a subject. Typically, allogeneic tissue or cells (e.g., functional cells, typically, islets of Langerhans) are transplanted and immunoisolated by an artificial membrane provided by macroencapsulation of the cells in a hydrogel such as an alginate matrix. The hydrogel macroencapsulating the islets is formed so as to have a planar, geometric configuration, e.g., a slab, a sheet, or a disc. Typically, the alginate structure has at least one substantially flat surface. The alginate comprises an ultrapure grade alginate and a defined composition that is cross-linked so as to encapsulate the cells or tissue segments in a hydrogel. Typically, the alginate slab houses islets at a density of 2,000-8,000 islets/cm^2, e.g., up to 6,000 islets/cm^2, typically, about 4,000 islets/cm^2. For example, if the flat macroencapsulating structure is 10 cm×10 cm, then it would contain 600,000 islets at a density of 6,000 islets/cm^2). Implanting the macroencapsulated slab of islets in a well-perfused area of the body, e.g., the subcapsular space of the kidney, supports transplantation and maintains viability of a dose of between 1,000 and 50,000 islets per kilogram body weight, e.g., between 3,000 and 6,000 islets per kilogram body weight, typically, around 5,000 islets per kilogram body weight. The alginate macroencapsulating the islets typically has a concentration of guluronic acid of less than 50% (e.g., between 40% and 47%) such that the slab is flexible enough to conform to the shape of the kidney and fit within the subcapsular space thereof, but strong enough to maintain its overall physical characteristics. Additionally, the alginate comprises a dry matter content that is greater than 1.5% (e.g., greater than 1.6%, typically, about 2.2% dry matter) such that the slab is strong and stable enough to withstand forces, e.g., including compression and shear stress, imparted thereto by the kidney and by the retinal capsule. Thus, the subcapsular space of the kidney supports a large number of macroencapsulated islets in a single, stable, slab.

In a specific example, 400,000 islets may be encapsulated in a slab having an area of 100 cm^2 and transplanted in the subcapsular space of the kidney of a human. Alternatively, two capsules each having an area of 50 cm^2 and each housing 200,000 islets may be implanted in the subcapsular space of a respective kidney.

(In this context, in the specification and in the claims, "slab" means any one of the planar, geometric configurations mentioned herein, e.g., slab, disc, sheet.)

Typically, the macroencapsulated islets slab provides a ratio of volume of islets to volume of alginate of at least 1:10 (i.e., 10% islets by volume), in contrast to the ratio of 1:100 (i.e., 1% islets by volume) in known microencapsulation techniques. In some applications of the present invention, the macroencapsulated islet slab comprises around 20% islets by volume. In microencapsulation techniques, a significantly large number of islets (i.e., between 10,000 and 20,000 islets per kilogram body weight) is transplanted within the body of the recipient. Such a large number of islets also increases the total volume of alginate encapsulating the islets, because microencapsulation inherently increases the total volume of alginate. Typically, the subcapsular space of the kidney cannot support such a volume of alginate combined with the volume of islets. In contrast, macroencapsulation techniques described herein reduce the total volume of alginate by about one order of magnitude while also typically reducing the therapeutic dose of islets (e.g., to 5,000 islets per kilogram body weight).

Under physiological conditions, the alginate is negatively charged. Additionally, under physiological conditions (e.g., physiological pH), most proteins are also negatively charged. Therefore, (a) in response to charge-charge interaction between the alginate and the proteins (e.g., antibodies and cytokines) of the recipient, the inward diffusion through the alginate of proteins of the recipient will be attenuated, and in some cases, substantially eliminated, while (b) outward diffusion of proteins, e.g., insulin, from the encapsulated islets will be accelerated, in response to charge-charge interaction between the alginate and the protein secreted from the islets.

In such a manner, the alginate slab functions as a membrane to immunoisolate the transplanted islets, and thus, the recipient mammal does not need to undergo immunosuppression (e.g., via administration of a drug) prior to and following implantation. The immunoisolation of the alginate slab depends on the molecular weight cutoff of the hydrogel of the slab, e.g., greater than 100 kDa. Additionally, the electrical attraction/repulsion of the particles passing through the alginate supplements the immunoisolation properties of the alginate slab. In some applications of the present invention, the alginate slab encapsulating the islets is surrounded by at least one semi-permeable membrane, e.g., a Biopore™ membrane, which reduces fibrosis and further immunoisolates the islets encapsulated in the alginate slab which may be exposed at the surface of the alginate slab. In some applications of the present invention, at least a portion of the semi-permeable membrane is incorporated or disposed within at least a portion of the alginate of the alginate hydrogel. In some applications of the present invention, a first surface of the alginate slab is immunoisolated by a first semi-permeable membrane, and a second surface of the alginate slab is immunoisolated by a second semi-permeable membrane. The primary role of the membrane surrounding the alginate is to prevent cell-cell contact between donor cells contained within the slab and host cytotoxic T-cells. Thus, a direct effect of killing of the donor cells by the host cells is prevented.

For some applications of the present invention, the alginate used to encapsulate the islets is supplemented with collagen. In some applications of the present invention, the macroencapsulation slab comprises at least one layer of medical grade collagen. In some applications of the present invention, the islets are disposed in the center of a primary alginate slab, and a supplementary alginate layer surrounds the encapsulated islets within the primary alginate slab. In such an application, a layer of medical grade collagen may be used in combination with the supplementary alginate layer. In some applications of the present invention, the collagen is used independently of or in combination with the semi-permeable membrane described hereinabove.

A method of preparing the alginate capsules is provided, for use in some applications of the invention.

In some applications of the present invention, a method of transplanting one or more macrocapsules in the body of a subject is provided. Typically, a needle comprising an alloy of wolfram and molybdenum is used to puncture through the fat pad surrounding the membranous renal capsule. The wolfram-molybdenum alloy of the needle provides (a) sufficient rigidity in order to puncture through the renal capsule and through the surrounding fat pad, and (b) sufficient flexibility to the needle in order to be maneuvered within the subcapsular space. The needle is agitated left and right in order to enlarge the hole created thereby and to create a pocket between the kidney and the renal capsule (i.e., within the subcapsular space of the kidney) for housing the alginate slab(s) encapsulating the islets. Once the slab(s) is introduced within the pocket, the renal capsule adheres to and envelopes the slab(s), thereby sealing the pocket created in the subcapsular space of the kidney without the need for sutures.

There is therefore provided, in accordance with some applications of the present invention of the present invention, apparatus, including:
 a plurality of islets; and
 a hydrogel configured to macroencapsulate the plurality of islets, the hydrogel being implantable in a subcapsular space of a kidney of a subject, and shaped to define a planar configuration.

In some applications of the present invention, the apparatus includes at least one semi-permeable membrane covering at least a portion of the hydrogel.

In some applications of the present invention, the plurality of cells has a density of 2,000-8,000 islets/cm^2.

In some applications of the present invention, the apparatus includes at least one semi-permeable membrane disposed at least in part within at least a portion of the hydrogel.

In some applications of the present invention, the hydrogel is configured to be implanted in the subcapsular space of the kidney using laparoscopy.

In some applications of the present invention, the hydrogel is configured to be removed from the subcapsular space of the kidney using laparoscopy.

In some applications of the present invention, the hydrogel includes constituents of extracellular matrix.

In some applications of the present invention, the hydrogel includes collagen.

In some applications of the present invention, the hydrogel includes laminin.

In some applications of the present invention, the hydrogel includes mesenchymal stem cells.

In some applications of the present invention, the plurality of islets includes 80,000-4,000,000 islets.

In some applications of the present invention, the plurality of islets includes 200,000-800,000 islets.

In some applications of the present invention, the hydrogel includes alginate, and the alginate has a concentration of guluronic acid of between 30% and 50%.

In some applications of the present invention, the concentration of guluronic acid is between 40% and 47%.

In some applications of the present invention, the alginate has a dry matter content of at least 1.6%.

In some applications of the present invention, the alginate has a dry matter content of at least 2.1%.

In some applications of the present invention, the alginate is cross-linked with strontium.

There is additionally provided, in accordance with some applications of the present invention of the present invention, a method, including:

providing a plurality of islets macroencapsulated in a hydrogel shaped to define a planar configuration; and implanting the macroencapsulated islets in a subcapsular space of a kidney of a subject.

In some applications of the present invention, providing the plurality of islets in the hydrogel includes providing the plurality of islets in a hydrogel that is covered at least in part by a semi-permeable membrane.

In some applications of the present invention, providing the plurality of islets in the hydrogel includes providing the plurality of islets in a hydrogel and in a semi-permeable membrane that is disposed at least in part within the hydrogel.

In some applications of the present invention, providing the plurality of islets in the hydrogel includes providing a plurality of islets having a density of 2,000-8,000 islets/cm^2.

In some applications of the present invention, implanting the macroencapsulated islets in the subcapsular space of the kidney includes implanting the macroencapsulated islets in the subcapsular space of the kidney using laparoscopy.

In some applications of the present invention, the method includes removing the macroencapsulated islets from the subcapsular space of the kidney using laparoscopy.

In some applications of the present invention, providing the plurality of islets in the hydrogel includes providing the plurality of islets in a hydrogel that includes constituents of extracellular matrix.

In some applications of the present invention, providing the plurality of islets in the hydrogel includes providing the plurality of islets in a hydrogel that includes collagen.

In some applications of the present invention, providing the plurality of islets in the hydrogel includes encapsulating the plurality of islets in a hydrogel that includes laminin.

In some applications of the present invention, providing the plurality of islets in the hydrogel includes providing the plurality of islets in a hydrogel that includes mesenchymal stem cells.

In some applications of the present invention, providing the plurality of islets in the hydrogel includes providing 80,000-4,000,000 islets.

In some applications of the present invention, providing the plurality of islets in the hydrogel includes providing 200,000-800,000 islets.

In some applications of the present invention, providing the plurality of islets in the hydrogel includes providing the plurality of islets in alginate having a concentration of guluronic acid of between 30% and 50%.

In some applications of the present invention, providing the plurality of islets in the alginate includes providing the plurality of islets in alginate having a concentration of guluronic acid of between 40% and 47%.

In some applications of the present invention, providing the plurality of islets in the alginate includes providing the plurality of islets in alginate having a dry matter content of at least 1.6%.

In some applications of the present invention, providing the plurality of islets in the alginate includes providing the plurality of islets in alginate having a dry matter content of at least 2.1%.

In some applications of the present invention, providing the plurality of islets in the alginate includes providing the plurality of islets in alginate that is cross-linked with strontium.

There is yet additionally provided, in accordance with some applications of the present invention of the present invention, a method, including:

providing a plurality of islets macroencapsulated in a hydrogel shaped to define a planar configuration; and implanting the macroencapsulated islets in at least one area of a body of a subject selected from the group consisting of: a liver of the subject, an area in a vicinity of a diaphragm of the subject, and an omental pouch of the subject.

There is further provided, in accordance with some applications of the present invention of the present invention, apparatus, including:

a plurality of islets having a density of 2,000-8,000 islets/cm^2;

an alginate structure having a planar configuration that macroencapsulates the plurality of islets, the structure configured to be implanted in a subcapsular space of a kidney of a subject, and having:

a longest dimension between 30 mm and 120 mm, a dry matter content of at least 1.6%, and a concentration of guluronic acid of between 40% and 50%.

In some applications of the present invention, the dry matter content of alginate in the alginate capsule is between 2.1% and 5.0%.

In some applications of the present invention, the concentration of guluronic acid is between 40% and 47%.

In some applications of the present invention, the plurality of islets includes 200,000-800,000 islets.

There is also provided, in accordance with some applications of the present invention of the present invention, a method, including:

providing a plurality of islets having a density of 2,000-8,000 islets/cm^2 macroencapsulated in an alginate structure having:

a planar configuration, a longest dimension between 30 mm and 120 mm, a dry matter content of at least 1.6%, and a concentration of guluronic acid of between 40% and 50%; and implanting in a subcapsular space of a kidney of a subject the alginate structure that macroencapsulates the plurality of islets.

In some applications of the present invention, providing the plurality of islets in the alginate structure includes providing the plurality of islets in an alginate structure having a dry matter content of between 2.1% and 5.0%.

In some applications of the present invention, providing the plurality of islets in the alginate structure includes providing the plurality of islets in an alginate structure having a concentration of guluronic acid between 40% and 47%.

In some applications of the present invention, providing the plurality of islets in the alginate structure includes providing 200,000-800,000 islets.

The present invention will be more fully understood from the following detailed description of applications thereof, taken together with the drawings, in which:

BRIEF DESCRIPTION OF THE DRAWINGS

FIGS. 1A-F are schematic illustrations of transplantation of macroencapsulated islets in a subcapsular space of a kidney, in accordance with some applications of the present invention of the present invention;

FIG. 2 is a graphical representation of experimental results showing blood glucose levels of six groups of rats each prior to and following transplantation of islets macroencapsulated in alginates having various G-contents, in accordance with some applications of the present invention of the present invention;

FIG. 4 is a graph of experimental results showing optimization of the density of islets macroencapsulated in alginate having a 46% G-content, in accordance with some applications of the present invention of the present invention.

DETAILED DESCRIPTION OF APPLICATIONS

Reference is now made to FIGS. 1A-F, which are schematic illustrations of a procedure 20 for transplantation of macroencapsulated islets in a subcapsular space 21 of a kidney 22, in accordance with some applications of the present invention. Islets are metabolically active and demand a large supply of oxygen. Once macroencapsulated, the islets are designated for implantation within the subcapsular space of the kidney, which is an area of the body adjacent to a vascular bed and is well perfused such that the area supports the oxygen needs of the highly-metabolic, macroencapsulated islets.

As has been shown in experiments detailed below, macroencapsulation of the islets in an alginate structure of planar configuration (e.g., a disc-shaped slab, a flat sheet, or any other generally planar shape) provides an efficient means of transplanting islets into the subcapsular space of the kidney.

Figure 1A:
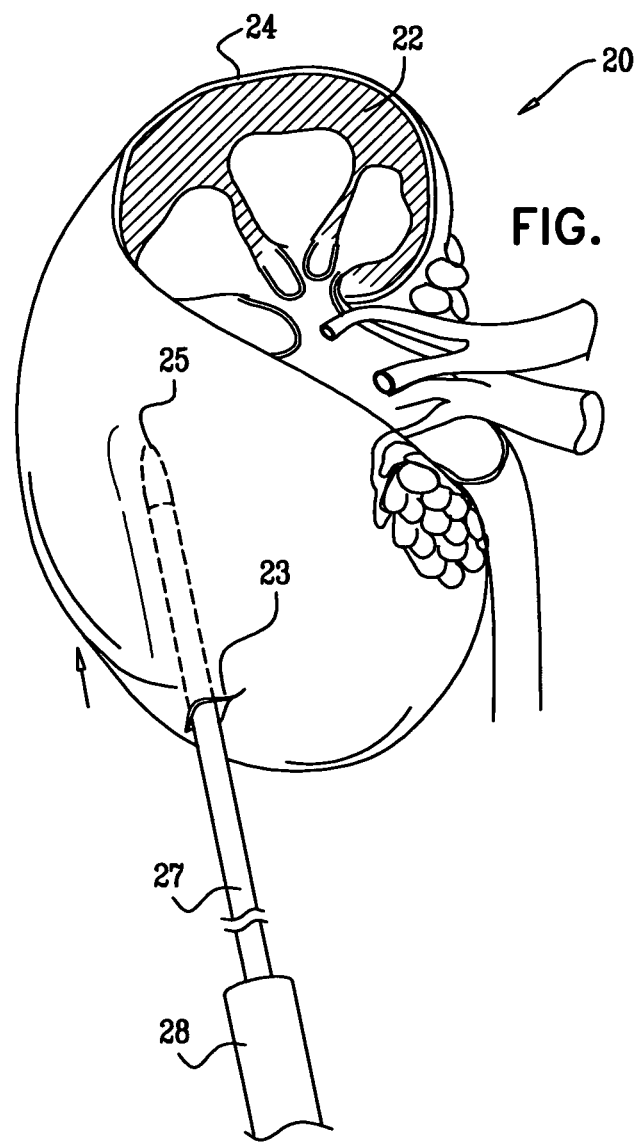

As shown in FIG. 1A, renal capsule 24 surrounding kidney 22 is perforated by a needle 27 comprising a wolfram-molybdenum alloy wire having a filed, blunt tip 25. Needle 27 is coupled to a handle 28, as shown. Through a hole 23 created in capsule 24 by needle 27, a distal portion of needle 27 is inserted in the subcapsular space of kidney 22, i.e., between kidney capsule 24 and the renal cortex, such that blunt end 25 of needle 27 is disposed at approximately the middle of the external surface of kidney 22.

Figure 1B:
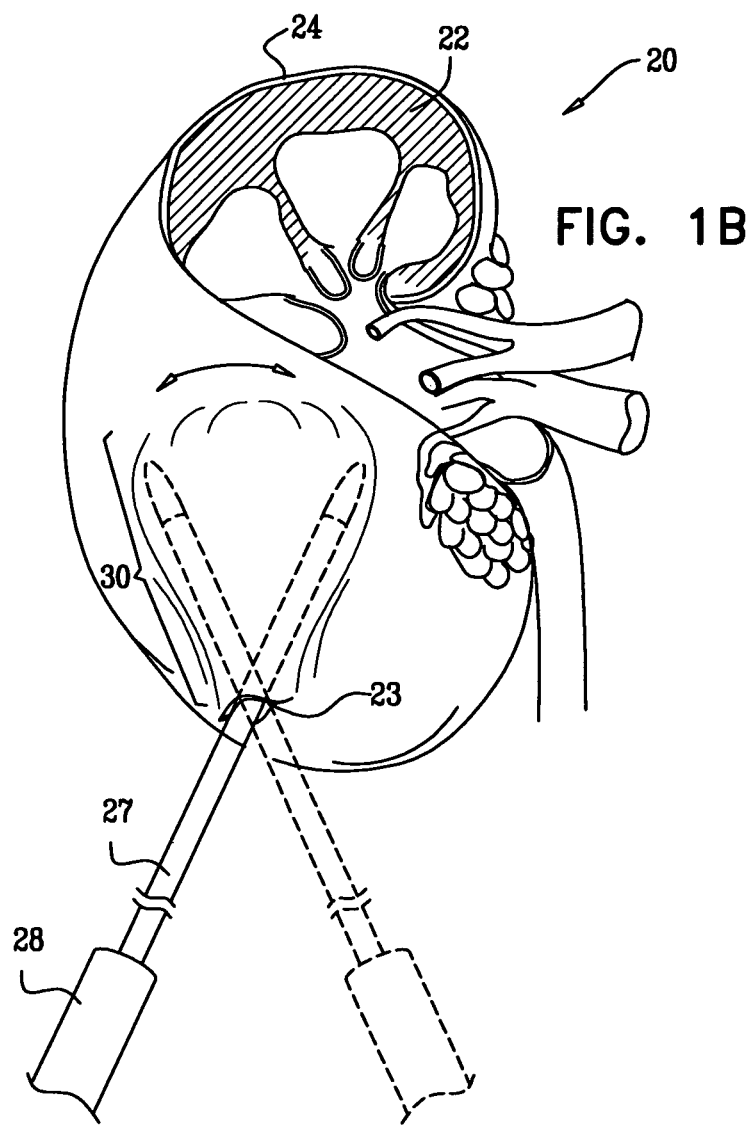

As shown in FIG. 1B, needle 27 is moved left and right and up and down, in the direction as indicated by the arrows, so that the distal portion of needle 27 moves within the subcapsular space of the kidney, thereby partially detaching capsule 24 from the external surface of the renal cortex in order to create a pocket 30 in the subcapsular space of kidney 22.

Figure 1C:
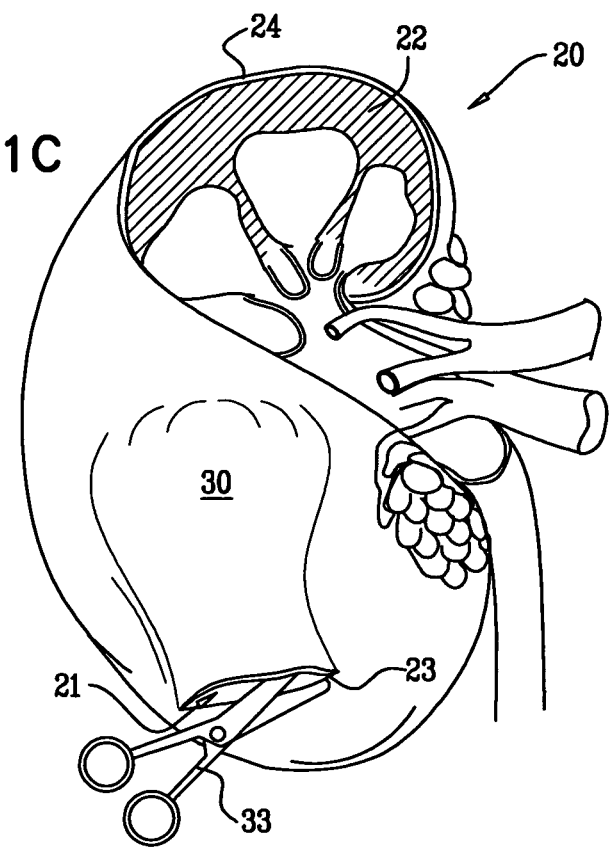

Reference is now made to FIG. 1C. Needle 27 is removed and hole 23 through which needle 27 was initially inserted into the subcapsular space is delicately enlarged using a cutting tool 33, such as scissors, a cold-blade scalpel or an electrical surgical tool. Tool 33 cuts a few millimeters of renal capsule 24 from hole 23, typically in both left and right directions therefrom.

Figure 1D:
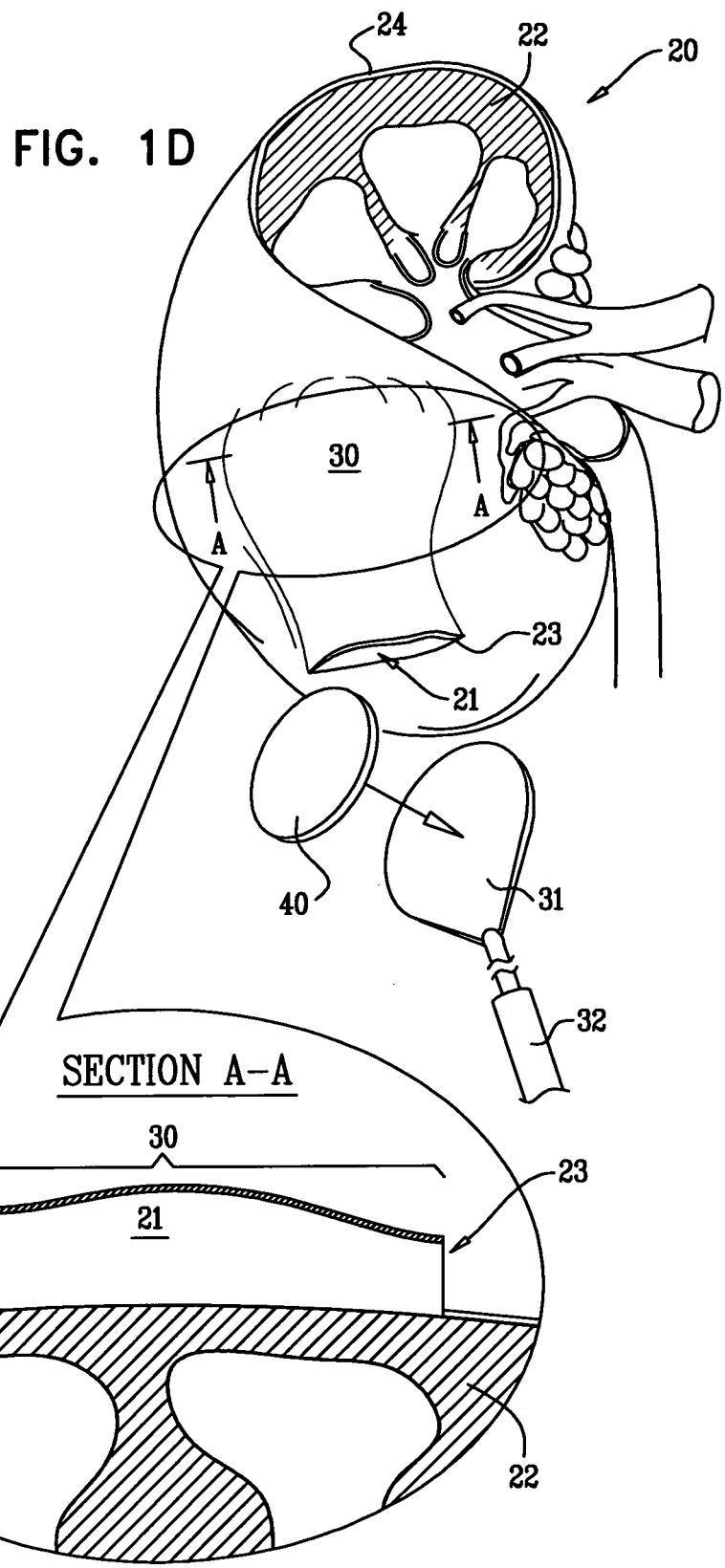

Reference is now made to FIG. 1D, which shows a cross-sectional illustration of pocket 30 created in subcapsular space 21 of kidney 22. An alginate slab 40 macroencapsulating the islets is placed on a planar flat surface 31 of a spatula device 32.

FIG. 1E shows planar surface 31 and slab 40 being inserted within pocket 40 created in subcapsular space 21 of kidney 22. As planar surface 31 and slab 40 are introduced within pocket 30, forceps or other gripping tools are used to raise the portion of renal capsule 24 that defines pocket 30 at hole 23. After planar surface 31 and slab 40 are placed within pocket 30, the forceps are disengaged from renal capsule 24 to allow it to rest upon slab 24.

Renal capsule 24 envelopes alginate slab 40 and planar surface 31 of spatula device 32. Typically, the planar configuration of the substantially flat alginate slab provides slab 40 with a large surface area, i.e., a combined surface area of an upper surface and a lower surface. The lower surface of slab 40 contacts the external surface of the renal cortex of while the upper surface of slab 40 contacts the lower (interior) surface of renal capsule 24. The surface area facilitates a large area of molecular diffusion and also a large area of adhesion of slab 40 to both capsule 24 and the external surface of the cortex of kidney 22. Cohesive tension between the fluid of renal capsule 24 and kidney 22 causes capsule 24 to envelop alginate slab 40 as renal capsule 24 reattaches itself to the external surface of the cortex of kidney 22. As alginate slab 40 is enveloped by renal capsule 24, planar surface 31 of spatula device 32 is extracted from within pocket 30, leaving behind alginate slab 40. Such cohesive tension holds alginate slab 40 in place within subcapsular space 21. Pocket 30 is, therefore, typically closed without the need for surgical sutures, resulting in a faster healing process. The abdomen of the subject is then closed by surgical sutures.

Typically, as is demonstrated by experimental results described hereinbelow, the composition of the alginate of 40-50% G-content (i.e., a high M-content, or concentration of mannuronic acid) and a dry matter content of greater than 1.6% (e.g., at least 2.1%, typically, between 2.1% and 5.0%), provides slab 40 with: (a) sufficient strength and mechanical resistance to withstand forces (e.g., including compression and shear stress) imparted thereto by the kidney and by the retinal capsule, and (b) sufficient flexibility to conform to the pocket created in the subcapsular space of kidney 22.

FIG. 1F shows alginate slab 40 macroencapsulating the islets disposed within the subcapsular space of kidney 22. As shown, slab 40 covers up to about ⅓ of the external surface of the cortex of kidney 22. It is to be noted that although one slab 40 is shown, two or more slabs 40 may be implanted within one kidney. Alternatively, one or more slabs 40 may be implanted within the subcapsular space of each of the two kidneys 22.

Thus, the surgical procedure preceding the transplantation of the alginate slab creates a pocket 30 that is bordered by the kidney cortex on one side and the capsular membrane on the other side.

Protocol of the Experiment

Islet Extraction:

Islets were extracted from 300 g male Lewis rats (obtained from Harlan, Israel) which were anesthetized with IV injection of xylazine/ketamine at doses of 10 mg or 90 mg per kilogram body weight. Islets were isolated from pancreata of the rats by the collagenase method using Serva NB8 and non-continuous Ficoll density gradient. The islets were then incubated for a period of one week in CMRL: RPMI medium (1:1; glucose concentration 8:47 mM) before being transplanted within syngeneic recipient rats.

During the first three days, the islets were cultured in a first incubator at a temperature of 27 C. The islets were then transferred to a second incubator and during the remaining days four days of the one-week culture period, the islets were cultured at a temperature of 37 C. In a series of experiments, and in accordance with some applications of the present invention, the inventors experimentally determined that for maintaining a high percent of viable islets at the end of the culture period, ambient temperature for the first three days of incubations is lowered by about 10 C, e.g., to 25-29 C.

It is to be noted that although a culture period of one week was utilized, the culture period may be 6-8 days, or outside of this range.

Diabetes Induction and Preparation for Transplantation:

About 10 days prior to transplantation of the encapsulated islets, diabetes was induced in recipient animals by IV injection of 85 mg/kg body weight (BW) Streptozotocin (Sigma, Cat No. S0130). The recipient rats weighted about 330 g each. The recipient rats were further monitored by measuring non-fasting blood glucose levels, and were deemed diabetic when their non-fasting measurements exceed 500 mg/dL for a period of more than three consecutive days.

In preparation for surgery, the non-fasting blood glucose level was reduced by subcutaneously implanting in the recipient rats an insulin-secreting pad (obtained from Linplant; LinShin Canada Inc). The rats were ready for the transplantation procedure when their non-fasting blood glucose levels decreased beyond 150 mg/dL for a period of three consecutive days.

On the day of encapsulated islet transplantation, the Linplant pad was removed from each rat, and respective alginate macrocapsules each containing 1,100 islets were transplanted into the subcapsular space of both kidneys.

Procedure

Preparation of Encapsulated Islets and Transplantation Thereof

Slab Preparation/Encapsulation of the Islets:

Islets were mixed with the alginate hydrogel to make total volume of 40 ul. Cross-linking within the alginate is performed using 70 mM SrCl2 (i.e., a total of 270 mOsm) for 10 minutes between 500 um stainless steel spacers of a hypodermic needle (BD Microlance®, 25G (0.5×16 mm).

The capsules were prepared using the following protocol:
1. Suspend the islets and remove supernatant from islets and add the alginate solution.
2. Mix the solution together with the suspended islets and draw the islet-alginate mixture into a silicone blunt tip.
3. Place the islet-alginate mixture into an alginate mold with a thickness of up to 500 um, mix and spread evenly.
4. Dip a sinter glass (Cat No. 3040/14M, Pyrex, UK) in SrCl2 solution and apply a mild vacuum for 20 minutes until bubbles do not appear.
5. Place the sinter glass on the alginate mold using 25 g/cm^2 of weight on top.
6. Remove the sinter glass.

Remove the alginate slab from the mold and incubate in a medium. The medium comprises a CMRL:RPMI (1:1) medium and calcium in a concentration of 1.5-2.0 mM. This medium is used in excess in order to wash away excess strontium and equilibrate the islets.

In some applications of the present invention, barium is combined together with the alginate mold, e.g., by using BrCl2 in addition to or instead of SrCl2 in step 4. In such some applications of the present invention, the barium combined with the alginate mold has a concentration of 20 mM and an osmolality similar to that of strontium, i.e., approximately 270 mOsm.

Transplantation Procedure:

Each of the recipient rats was anesthetized and the abdominal cavity was opened along the linea alba. The intestine was retracted with wet pad gauze to expose the kidney area. The implantation procedure of the encapsulated islets in the body of the rat is similar to the procedure for implantation of the encapsulated islets in the body of a human, as described hereinabove with reference to FIGS. 1A-F.

Figure 3:
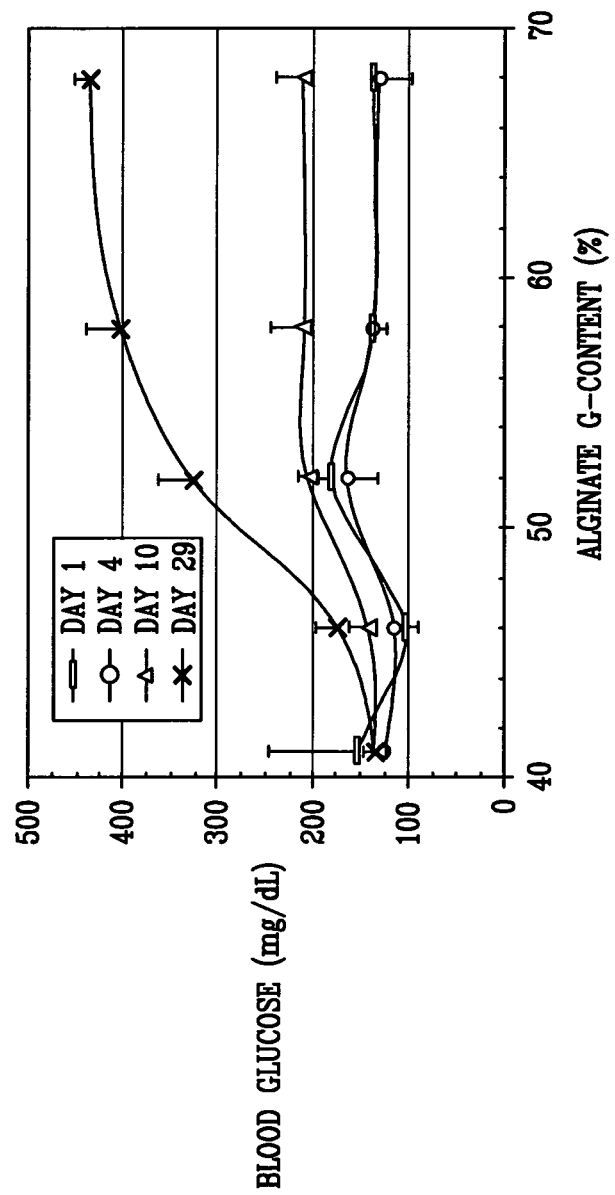
FIG. 3 is a graphical representation of experimental results showing blood glucose levels of six groups of rats each at 1, 4, 10, and 29 day(s) following transplantation of islets macroencapsulated in alginates having various G-contents, in accordance with some applications of the present invention of the present invention.

Reference is now made to FIGS. 2 and 3, which are graphical representations of experimental 3-day moving average results showing non-fasting blood glucose levels of rats prior to and following transplantation of islets macro-encapsulated in alginates having various G-contents, in accordance with some applications of the present invention. Groups of islets were extracted from donor rats and encapsulated in respective alginate macrocapsules having various concentrations of guluronic acid (i.e., G-content). The alginate macrocapsules containing the islets were then transplanted in the subcapsular space of kidneys of syngeneic recipient rats (in a manner as described hereinabove with respect to FIGS. 1A-F). The capsules are substantially disc-shaped and have a diameter of less than 8 mm, e.g., 7.5 mm, and a height of around 0.5 mm.

The alginate macrocapsules containing the islets were implanted in the subcapsular space of the kidney in order to create an artificial pancreas. The subcapsular space: (1) accommodates the morphology of the large capsule containing between 1,000 and 2,500 islets, e.g., typically between 1,100 and 1,750 islets, and (2) provides vasculature for oxygen perfusion through the alginate capsule and toward the encapsulated islets.

The alginate structure provides a large surface area for adhesion to the subcapsular space of the kidney and facilitates prevention of rejection by the host's immune system. By this technique, allogeneic, living islets are encapsulated in a protective alginate membrane that allows insulin to be secreted, yet prevents cytotoxic cells and complement components of the acquired immune system from reaching the islets, causing rejection of the cells. This allowance of insulin secretion through the capsule helps facilitate controlling and maintaining normal glycemic conditions in the diabetic host.

An experiment was conducted in order to test which G-content of the alginate optimizes glycemic control in the body of the rat. Six groups of islets were encapsulated in respective alginate slabs having various G-contents. The following alginates were used to encapsulate the islets:

1. UltraPure (UP) KELTON® (obtained from ISP (UK)) having a G-content of 41% with a dry matter content of 2.2%;
2. Pronova UP MVM alginate (high mannuronic content alginate) (obtained from Novamatrix, Norway) having a G-content of 46% with a dry matter content of 2.2%;
3. A roughly 1:1 mix of Pronova UP MVM alginate (obtained from Novamatrix, Norway) and Pronova UP MVG alginate (a high guluronic content alginate) (obtained from Novamatrix, Norway) having a G-content of 52% with a dry matter content of 2.2%;
4. UP MANUGEL® (obtained from ISP (UK)) having a G-content of 58% with a dry matter content of 1.5%;
5. Pronova UP (obtained from Novamatrix, Norway), MVG having a G-content of 68% with a dry matter content of 1.5%; and
6. Control alginate—Pronova Strl (sterile) SLG-100 alginate (obtained from Novamatrix, Norway) having a G-content of 69% with a dry matter content of 1.5%.

The capsules were then implanted in the subcapsular space of the kidneys of the host rats. Following implantation, the non-fasting blood glucose levels of the host rats were monitored daily. As shown hereinbelow in graphical representations of the monitored data (with reference to FIGS. 2-4), the alginates having a lower G-content (i.e., 41% and 46% guluronic acid) generally maintained normal glycemic conditions (i.e., blood glucose levels of around 120-170 mg/dL) in the rats over a prolonged period of time (i.e., 30 days). Additionally, for alginates having a higher G-content, the non-fasting blood glucose levels of the respective rats were elevated beyond normal glycemic conditions within a few days (i.e., between 1 and 10 days) following transplantation of the capsules. Furthermore, high mannuronic acid alginates having a dry matter content that is greater than 1.5% (e.g., greater than 1.6%, particularly greater than 2.0%), exhibit sustained normoglycemia over a period of 30 days, and the implanted slabs retained their overall physical structure. Typically, the alginate has a dry matter content of 2-2.5% (e.g., 2.2%, as shown). This is because a dry matter content of 2.2% strengthens alginates having lower G-contents, e.g., 41% and 46%. Conversely, alginates having a dry matter content of 1.5% together with a G-content of greater than or equal to 52% exhibited poor regulation of glycemic conditions in the rats.

Results

Efficiency of Glycemic Control Provided by Islets Encapsulated in Alginates Having Various G-Contents:

Alginic acid is a linear co-polymer composed of linked (M)-beta-D-mannuronic acid and (G)-alpha-L-guluronic acid residues. Alginate polymer chains are made up of three types of regions. G-blocks are linear stretches of G-monomers, M-blocks are linear stretches of M-monomers, and MG blocks are stretches of MG- or GM-dimers along the polymer chain. Alginate polymers differ from each other on the basis of average molecular weight of the non-cross linked polymer, relative ratio between the G and M monomers, and average length of the G-blocks. Alginates function as hydrogels following cross-linking by metal ions at ambient temperature. Binding of divalent cations to alginate is highly selective, and the affinities increase in the order of Ba>Sr>Ca>>Mg.

Alginate capsules for transplantation within the subcapsular space of the kidney should have: (a) sufficient strength and mechanical resistance to withstand the forces, e.g., including compression and shear stress, imparted thereto by the kidney and by the retinal capsule, and (b) sufficient flexibility to conform to the pocket created in the subcapsular space of the kidney (described hereinabove with reference to FIGS. 1A-F).

Additionally, the gel surface of the alginate acts as a semi-permeable membrane, restricting passage therethrough of alginate molecules. In order to prevent swelling of the alginate, which leads to increased porosity and disruption of the gel, the alginate is cross-linked with barium or strontium and not calcium.

Thus, alginates of different G-contents and dry matter contents were tested for their ability to support long term glycemic control in chemically diabetic rats following transplantation of encapsulated islets in the subcapsular space of the kidney.

FIG. 2 is a graphical representation of experimental 3-day moving average results showing non-fasting blood glucose levels of rats prior to and for a period of 30 days following transplantation of islets macroencapsulated in alginates having various G-contents. This experiment was conducted on six groups of rats, and each group contained either 4, 5, or 6 rats. As described hereinabove, diabetes was chemically induced in the rats such that the non-fasting blood glucose of the rats exceeds 500 mg/dL for five days prior to transplantation. Prior to transplantation, an insulin patch was implanted in each of the six rats so as to reduce the blood glucose level to the physiological level, i.e., between 120-170 mg/dL.

On day 0, each of the capsules described hereinabove was implanted in the subcapsular space of a respective rat. The alginates having a G-content of 41% and 46% maintained the non-fasting blood glucose level below 200 mg/dL over a 30 day period of time. That is, the lower G-content alginate generally sustained functionality of the cells and facilitated oxygen transport toward the cells and insulin transport from the cells.

As shown, the rate of increase in non-fasting blood glucose levels rises with increasing G-content.

Furthermore, the experiment showed the efficiency of using ultrapure alginate over sterile alginate. The experiment demonstrated the relative abilities of ultrapure alginates and sterile alginates to maintain non-fasting blood glucose levels at physiological conditions. A comparison was made between: (1) the control alginate slab (i.e., the Pronova SLG-100, or Strl (sterile), alginate (obtained from Novamatrix, Norway) having a G-content of 69% with a dry matter content of 1.5%) and (2) the Pronova ultrapure alginate slab (obtained from Novamatrix, Norway) having a G-content of 68% with a dry matter content of 1.5%. As indicated by the curves of FIG. 2, the ultrapure alginate demonstrated more efficient regulation of non-fasting blood glucose levels relative to the regulation of non-fasting blood glucose levels demonstrated by the sterile alginate.

FIG. 3 shows non-fasting blood glucose levels of the six groups each containing either 4, 5, or 6 rats at 1, 4, 10, and 29 days following implantation. Data for the graph shown in FIG. 3 are taken from data for the graph shown in FIG. 2. As shown in FIG. 3, the alginates having the 41% and 46% G-content maintained the non-fasting blood glucose levels below about 150 mg/dL for the entire time period.

The higher G-content alginates exhibit elevating blood glucose levels toward day 29.

FIG. 4 is a graph of experimental results showing optimization of the density of islets macroencapsulated in alginate having a 46% G-content, in accordance with some applications of the present invention. The three experiments were conducted to determine an efficient density of islets that could be safely encapsulated in a given alginate slab.

In a first experiment, 2,500 islets (i.e., a density of 5,700 islets/cm^2, corresponding to a dose of around 7,500 islets/kg body weight) were encapsulated in the 46% G-content alginate disc-shaped slab having a diameter of 7.5 mm and a height of 0.5 mm and were transplanted into the subcapsular space of the kidney of a rat weighing around 330 g. In a second experiment, 1,750 islets (i.e., a density of 4,000 islets/cm^2, corresponding to a dose of around 5,300 islets/kg body weight) were encapsulated in the 46% G-content alginate capsule and transplanted into a rat weighing around 330 g. In a third experiment, two capsules each containing 1,100 islets (i.e., a density of 2,500 islets/cm^2, corresponding to a dose of around 6,600 islets/kg body weight), were transplanted into a rat weighing around 330 g.

As shown, encapsulating fewer islets in a single alginate slab having a diameter of 7.5 mm and a height of 0.5 mm maintained the blood glucose level roughly under 200 mg/dL over a thirty day period of time, while encapsulating a relatively large number of islets in the alginate slab caused (or did not prevent) an increase in the blood glucose level over a thirty day period of time. Encapsulating 1,100 islets in each of two alginate slabs (each having a low density relative to slabs having a diameter of 7.5 mm and a height of 0.5 mm and containing 1,750 and 2,500 islets, respectively) maintained the blood glucose level below 200 mg/dL over a period of 30 days.

From the experiment described above, it was deduced that the following parameters provide efficient transplantation and cell viability over a long period of time (i.e., at least 30 days): (a) the alginate has a G-content of between 40% and 47%, and (b) the slab has a density of less than 6,000 islets/cm^2 (e.g., less than 5,700, typically, a density up to about 4,000 islets/cm^2). For a rat, it was determined that an alginate slab having (a) a diameter of between 7 mm and 10 mm (b) a width of between 300 um and 500 um, and (C) a volume of 40 ul, maintains physiological glucose levels when it macroencapsulates between 1,000 and 2,000 islets, e.g., between 1,100 and 1,750, at a density of up to 4,000 islets/cm^2. Thus, the rats receive islets at a dose of around 5,000 islets per kilogram body weight.

For the purposes of implanting islets in the subcapsular space of the kidney of a human, an alginate structure of planar configuration (e.g., a disc-shaped slab, a flat sheet, or any other generally planar shape) having a longest dimension of between 30 mm and 120 mm, is capable of encapsulating the islets at a density between 2,000 and 8,000 islets/cm^2, e.g., 4,000 islets/cm^2. For example, an alginate slab having an area of 100 cm^2 (e.g., 10 cm×10 cm, or corresponding suitable circular or elliptical dimensions) and a volume of 40 ml is able to encapsulate around 600,000 islets at a dose of around 5,000 islets per kilogram of body weight. Additionally, the subcapsular space of the human kidney is capable of supporting a capsule of 100 cm^2. In some applications of the present invention, two slabs each having a dimension of 50 cm^2 and a volume of 20 ml may be used to each encapsulate 200,000 islets. Typically, the therapeutic dose of islets transplanted in a human is up to 10,000 islets per kilogram body weight, e.g., typically, 5,000 islets per kilogram body weight. The slab typically has a width of between 300 um and 500 um.

Typically, microencapsulation techniques require a large dose of islets, e.g., between 10,000 and 20,000 islets per kilogram body weight. With macroencapsulation techniques described herein for transplanting islets into the subcapsular space of the kidney, a significantly smaller dose (e.g., up to 10,000 islets per kilogram body weight, typically, 5,000 islets per kilogram body weight) relative to the dose required in microencapsulation techniques (e.g., between 10,000 and 20,000 islets per kilogram body weight) restores and maintains normal glycemic conditions in the body. Furthermore, fewer islets (e.g., 400,000 islets, which is between 20% and 40% of the number of islets in a pancreas) are extracted from at least a single donor.

It is to be noted that the scope of the present invention includes the encapsulation of functional cells other than islets of Langerhans cells, e.g., dopaminergic cells, hepatic cells, adrenal cortical cells, or testicular or ovarian cells. It is to be further noted that the scope of the present invention includes the transplantation of the macroencapsulated islets into areas other than the subcapsular space of the kidney, e.g., in the peritoneum, in the omental pouch, under the diaphragm, in muscles, or in organs such as the spleen, liver, etc. It is to be yet further noted that the scope of the present invention includes encapsulating cells for xenogeneic transplantation.

It is to be further noted that the scope of the present invention includes the macroencapsulation, together with the islets, of adjuvant cells, feeder cells, nurse cells, antioxidants, trophic factors, and/or extracellular matrix (ECM), e.g., collagen, fibrinogen, laminin, and tenascin, together with the islets. For example, mesenchymal stem cells (MSC) macroencapsulated together with the islets contribute to islet performance in allogeneic transplantation of islets. In some applications of the present invention, the mesenchymal stem cells comprise stem cells configured for differentiation into pancreatic cells.

It is to be yet further noted that the scope of the present invention includes the implantation, retrieval, and replacement of the alginate slabs from the subcapsular space of the kidney using laparoscopy, by way of illustration and not limitation.

It is to be additionally noted that alginate/hydrogel structures that are configured for implantation in the subcapsular space of the kidney may be configured for macroencapsulating 80,000-4,000,000 islets, e.g., 200,000-800,000 islets, for example, 375,000-625,000 islets.

It is also noted that islets may be macroencapsulated in a hydrogel other than alginate. For example, the islets may be macroencapsulated in a polyvinyl acetate (PVA) hydrogel.

For some applications of the present invention, techniques described herein are practiced in combination with techniques described in one or more of the references cited in the Background section of the present patent application.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:
1. A method for controlling the blood glucose levels in a subject in need thereof, comprising:
   a. providing an implantable device having pancreatic islets containing insulin-producing cells in an amount sufficient to maintain blood glucose levels at a normal level in the subject, macroencapsulated in a three dimensional hydrogel, wherein the three dimensional hydrogel has a planar configuration and has a thickness from 300 microns to 500 microns wherein the amount sufficient to maintain blood glucose levels at a normal level in the subject is a density from 27,000 islets/cm$^3$ to 43,750 islets/cm$^3$; and b. implanting the implantable device in the subject, wherein following implantation, the implantable device maintains blood glucose levels at a normal level in the subject for at least 20 days.

2. The method according to claim 1, wherein the three dimensional hydrogel is covered at least in part by a semi-permeable membrane.

3. The method according to claim 1, wherein the pancreatic islets containing insulin-producing cells are provided in three-dimensional hydrogel and in a semi-permeable membrane that is disposed at least in part within the three-dimensional hydrogel.

4. The method according to claim 1, wherein the implantable device is implanted in the subcapsular space of the kidney.

5. The method according to claim 4, further comprising removing the implantable device from the subcapsular space of the kidney using laparoscopy.

6. The method according to claim 1, wherein the three dimensional hydrogel comprises constituents of extracellular matrix.

7. The method according to claim 1, wherein the three dimensional hydrogel comprises collagen.

8. The method according to claim 1, wherein the three dimensional hydrogel comprises laminin.

9. The method according to claim 1, wherein the three dimensional hydrogel comprises alginate having a concentration of guluronic acid of between 30% and 50%.

10. The method according to claim 9, wherein the alginate comprises alginate having a concentration of guluronic acid of between 40% and 47%.

11. The method according to claim 9, wherein the alginate comprises alginate having a dry matter content of at least 1.6%.

12. The method according to claim 9, wherein the alginate comprises alginate having a dry matter content of at least 2.1%.

13. The method according to claim 9, wherein the alginate comprises alginate that is cross-linked with strontium.

14. The method according to claim 12, wherein the alginate comprises alginate having a dry matter content of between 2.1% and 5.0%.

15. The method according to claim 1, wherein implanting comprises implanting the implantable device in an area of a body of the subject selected from the group consisting of: a subcapsular space of a kidney of the subject, a liver of the subject, an area in a vicinity of a diaphragm of the subject, and an omental pouch of the subject.

16. The method according to claim 9, wherein the alginate comprises alginate that is cross-linked with barium.

* * * * *